US012765763B2

(12) United States Patent
Ben-Nathan et al.

(10) Patent No.: US 12,765,763 B2
(45) Date of Patent: Oct. 20, 2026

(54) CERVICAL INSPECTION DEVICE, METHODS OF CONTROL THEREOF, AND CERVICAL SAMPLING BRUSH

(71) Applicant: LBN INNOVATIONS LIMITED, Ealing (GB)

(72) Inventors: Louise Ben-Nathan, Ealing (GB); Alex Blondeck, Usk (GB); Gary Badham, Usk (GB); Mark Helmich, Usk (GB)

(73) Assignee: LBN Innovations Limited, London (GB)

( * ) Notice: Subject to any disclaimer, the term of this patent is extended or adjusted under 35 U.S.C. 154(b) by 187 days.

(21) Appl. No.: 18/698,707

(22) PCT Filed: Oct. 6, 2022

(86) PCT No.: PCT/GB2022/052521

§ 371 (c)(1), (2) Date: Apr. 4, 2024

(87) PCT Pub. No.: WO2023/057755

PCT Pub. Date: Apr. 13, 2023

(65) Prior Publication Data

US 2024/0398222 A1 Dec. 5, 2024

(30) Foreign Application Priority Data

Oct. 7, 2021 (GB) ..................................... 2114384

(51) Int. Cl.
*A61B 5/00* (2006.01)
*A61B 1/00* (2006.01)
(Continued)

(52) U.S. Cl.
CPC .......... *A61B 1/303* (2013.01); *A61B 1/00066* (2013.01); *A61B 1/00071* (2013.01);
(Continued)

(58) Field of Classification Search
CPC . A61B 1/303; A61B 1/00066; A61B 1/00071; A61B 1/00142; A61B 1/018;
(Continued)

(56) References Cited

U.S. PATENT DOCUMENTS 3,626,928 A * 12/1971 Barringer ........... A61B 10/0291 604/38
3,636,940 A * 1/1972 Gravlee .................. A61M 1/77 604/38
(Continued)

FOREIGN PATENT DOCUMENTS

CH 718241 A2 * 7/2022 ............. A61B 1/303
CN 110381809 B * 6/2022 ............... A61B 1/32
(Continued)

OTHER PUBLICATIONS

International Preliminary Report on Patentability re International Application No. PCT/GB2022/052521 dated Nov. 8, 2023 (36 pages).

(Continued)

*Primary Examiner* — May A Abouelela
(74) *Attorney, Agent, or Firm* — Aurora Consulting LLC; Ashley Sloat

(57) ABSTRACT

A cervical inspection device (610) for performing a cervical smear test is provided. The device (610) has a tubular body (612) having a first end (614) which is engagable by an operator and a second end (616) which is insertable into a patient's vaginal canal, the tubular body (612) having a central bore (620) which extends along its longitudinal axis for receiving a cervical sampling brush (622) therethrough. There is also an expansion element (630) at or adjacent to the second end (616) of the tubular body (612) and control means operable from the first end (614) of the tubular body (612) for selectably expanding and/or contracting the expansion element (630). The expansion element (630) forms a
(Continued)

protective region beyond the central bore (620) in an expanded condition thereof for the said cervical sampling brush (622) to move through during a cervical smear test.

19 Claims, 20 Drawing Sheets

(51) Int. Cl.
*A61B 1/018* (2006.01)
*A61B 1/04* (2006.01)
*A61B 1/06* (2006.01)
*A61B 1/303* (2006.01)
*A61B 10/02* (2006.01)

(52) U.S. Cl.
CPC .......... *A61B 1/00142* (2013.01); *A61B 1/018* (2013.01); *A61B 1/04* (2013.01); *A61B 1/06* (2013.01); *A61B 10/0291* (2013.01); *A61B 2010/0216* (2013.01)

(58) Field of Classification Search
CPC ......... A61B 1/04; A61B 1/06; A61B 10/0291; A61B 2010/0216; A61B 1/00085; A61B 2010/0074; A61B 10/02; A61B 1/32; A61M 29/02
See application file for complete search history.

(56) References Cited

U.S. PATENT DOCUMENTS 3,828,765 A * 8/1974 McDonald ......... A61B 10/0291 600/573
4,054,127 A * 10/1977 Milan ................ A61B 10/0291 600/570
4,662,381 A * 5/1987 Inaba ................ A61B 10/0291 600/569
4,754,764 A * 7/1988 Bayne ................ A61B 10/0291 15/207.2
4,762,133 A * 8/1988 Bayne ................ A61B 10/0291 600/572
4,873,992 A * 10/1989 Bayne ................ A61B 10/0291 D4/133
5,191,899 A * 3/1993 Strickland .......... A61B 10/0291 600/572
5,279,307 A * 1/1994 Mohajer ............ A61B 10/0291 600/570
5,370,128 A * 12/1994 Wainwright ....... A61B 10/0291 600/569
5,445,164 A * 8/1995 Worthen ............ A61B 10/0045 600/572
8,968,213 B2 * 3/2015 Roush ................ A61B 10/0233 600/569
9,044,213 B1 * 6/2015 Lonky ................ A61B 10/0291
9,468,367 B2 * 10/2016 Ouyang ............. A61B 1/00103
9,687,142 B1 * 6/2017 Lieberman ......... A61B 1/00135
9,913,577 B2 * 3/2018 Swift ....................... A61B 1/32
10,201,332 B1 * 2/2019 Lonky .................... A61B 10/02
11,172,815 B2 * 11/2021 Magno ..................... A61B 1/32
2001/0023321 A1 * 9/2001 Gombrich .......... A61B 10/0291 600/572
2002/0161313 A1 * 10/2002 Sak .................... A61B 10/0045 600/569
2002/0165467 A1 11/2002 Rutenberg
2003/0028123 A1 * 2/2003 Pevoto ............... A61B 10/0045 600/572
2003/0120176 A1 * 6/2003 Reeves ............. A61B 10/0045 600/562
2003/0225313 A1 * 12/2003 Borodulin .............. A61B 1/303 600/220
2005/0256426 A1 * 11/2005 Brugge .................. A61B 10/04 600/569
2006/0200043 A1 * 9/2006 Jannetty ............. A61B 10/0045 600/570
2007/0073186 A1 * 3/2007 Decker .............. A61B 10/0045 600/570
2007/0106174 A1 * 5/2007 Sanders ................. A61B 17/42 604/38
2008/0188769 A1 * 8/2008 Lu .......................... A61B 10/02 600/569
2009/0062690 A1 * 3/2009 Kim ................... A61B 10/0291 600/573
2009/0062691 A1 * 3/2009 Kim ................... A61B 10/0291 600/573
2009/0275859 A1 * 11/2009 Kim ................... A61B 10/0291 600/569
2010/0124780 A1 * 5/2010 Larkin ............... A61B 10/0291 435/307.1
2010/0125223 A1 * 5/2010 Roan ...................... A61B 10/02 600/569
2010/0249649 A1 * 9/2010 Larkin ................... A61B 10/02 600/569
2011/0021950 A1 * 1/2011 Daniels .................. A61B 10/02 600/562
2011/0172557 A1 * 7/2011 Lonky ................ A61B 10/0291 600/569
2011/0190579 A1 * 8/2011 Ziarno ............... A61B 1/00096 600/109
2012/0289858 A1 * 11/2012 Ouyang ............. A61B 1/00101 600/562
2013/0066233 A1 * 3/2013 Klein ................. A61B 10/0291 600/572
2013/0131457 A1 * 5/2013 Seckin ............... A61B 17/4241 600/235
2013/0158429 A1 * 6/2013 Lee-Sepsick ...... A61B 10/0275 600/570
2013/0172778 A1 * 7/2013 Teschendorf ...... A61B 10/0291 600/562
2013/0267870 A1 * 10/2013 Lonky .................... A61B 10/02 600/569
2015/0057565 A1 * 2/2015 Mazzoli, Jr. ....... A61B 10/0291 600/564
2015/0182205 A1 * 7/2015 Millard .............. A61B 1/00142 600/424
2015/0272554 A1 * 10/2015 McSherry ............... A61F 13/38 600/572
2016/0015252 A1 * 1/2016 Piskun ............... A61B 1/00087 600/104
2016/0106309 A1 * 4/2016 Begg .................. A61B 1/00071 600/160
2016/0227994 A1 * 8/2016 Gotsch ................. A61B 1/0684
2016/0331357 A1 * 11/2016 Czarnecki .......... A61B 10/0291
2016/0367148 A1 * 12/2016 Froloff ................. A61B 1/0005
2017/0042518 A1 * 2/2017 Sak .................... A61B 10/0291
2017/0071583 A1 * 3/2017 McSherry .............. C12M 33/02
2017/0079520 A1 * 3/2017 Huang ................... A61B 1/045
2017/0119240 A1 * 5/2017 Millard .................. A61B 34/20
2017/0303903 A1 10/2017 De et al.
2018/0028164 A1 * 2/2018 Gombrich .......... A61B 10/0291
2018/0078242 A1 * 3/2018 Aghdam ............ A61B 10/0096
2018/0161021 A1 * 6/2018 Malanowska-Stega ..................... A61B 10/02
2019/0104932 A1 * 4/2019 Truckai .......... A61B 17/320016
2019/0150725 A1 * 5/2019 Ramanujam ........... A61B 1/015
2019/0246884 A1 * 8/2019 Lu ...................... G02B 23/2484
2019/0275306 A1 * 9/2019 Kamler ................ A61B 1/0014
2020/0093467 A1 * 3/2020 Lonky .................... A61B 17/32
2020/0129047 A1 * 4/2020 Tingvatn ............ A61B 1/00096
2020/0229802 A1 * 7/2020 Lonky .................... A61B 10/02
2020/0315444 A1 * 10/2020 Ramanujam ........... A61B 1/307
2021/0076925 A1 * 3/2021 Rhee ........................ A61B 1/01
2021/0100539 A1 * 4/2021 Cagnes .............. A61B 10/0291
2021/0137506 A1 5/2021 Thakor
2021/0236702 A1 * 8/2021 Begg ....................... A61M 1/90
2021/0259527 A1 * 8/2021 Craig ................. A61B 1/00057
2021/0307591 A1 * 10/2021 Ouyang ............. A61B 1/00066
2021/0315552 A1 * 10/2021 Kabaria ................ B33Y 80/00
2021/0369094 A1 * 12/2021 Chin ........................ A61B 1/05

(56) References Cited

U.S. PATENT DOCUMENTS

2022/0000339 A1* 1/2022 Nwanna-Nzewunwa ................... G16H 40/63
2022/0047152 A1* 2/2022 Bob ........................ A61B 1/018
2022/0054113 A1* 2/2022 Snyder ............... A61B 10/0291
2022/0061650 A1* 3/2022 Tingvatn ................ A61B 1/303
2022/0087512 A1* 3/2022 Lalli .................... A61B 5/4337
2022/0218318 A1* 7/2022 Ayagh ................ A61B 1/00087
2022/0240903 A1* 8/2022 Edmunds ........... A61B 10/0291
2022/0280029 A1* 9/2022 Nelson ............... A61B 1/00066
2022/0287694 A1* 9/2022 Neblett-Blackmon ...................... A61B 10/0291
2023/0073028 A1* 3/2023 Malanowska-Stega ..................... A61B 10/0045

FOREIGN PATENT DOCUMENTS

EP 3053506 A1 * 8/2016 ............. A61B 1/303
JP 2023540501 A * 9/2023 ............. A61B 1/018
KR 1020230011731 B1 8/2023
WO 2017124755 A1 7/2017
WO WO-2017181218 A1 * 10/2017 ............. A61B 1/303
WO 2020096666 A2 5/2020
WO WO-2022058779 A1 * 3/2022 ............. A61B 1/303

OTHER PUBLICATIONS

International Search Report re PCT/GB2022/052521 mailed Feb. 13, 2023 (5 pages).
IPO Combined Search Report and Examination Report re Application No. GB2311820.1, date of search Aug. 8, 2023 (4 pages).
IPO Communication—Examination Report and Intention to Grant re Application No. GB2114384.7 dated Jul. 12, 2023 (2 pages).
IPO Search Report under Section 17 re Application No. GB2114384.7, date of search Jun. 17, 2022 (1 page).
Partial International Search re PCT/GB2022/052521 dated Jan. 9, 2023 (8 pages).
Written Opinion of the International Preliminary Examining Authority re International No. PCT/GB2022/052521 dated Aug. 22, 2023 (4 pages).

* cited by examiner

Figure 5A
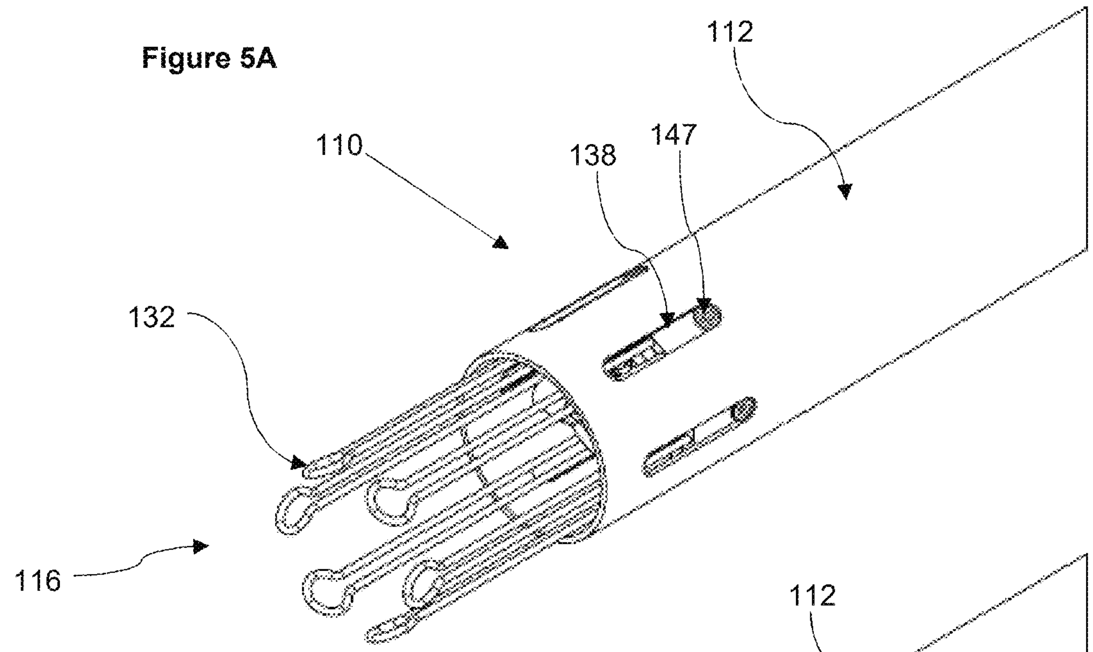
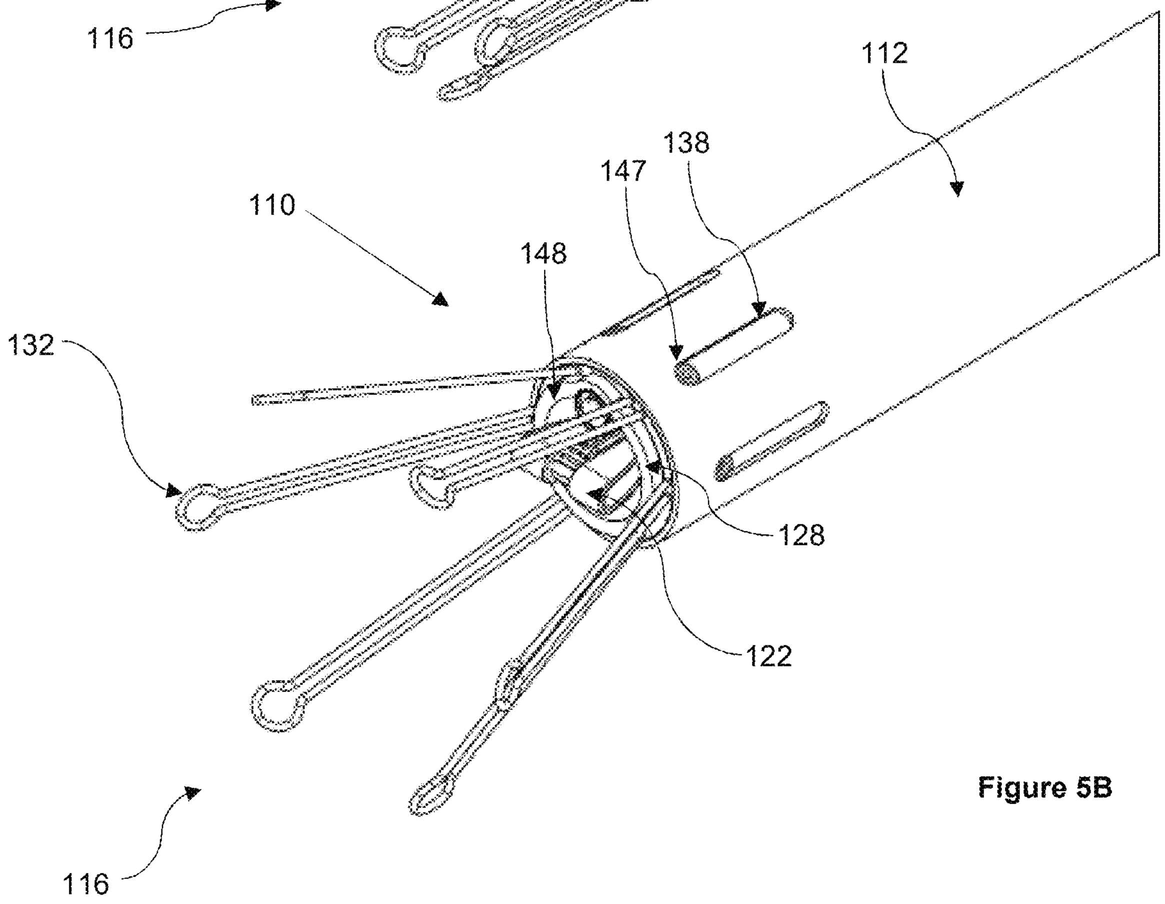
Figure 5B

Figure 13A
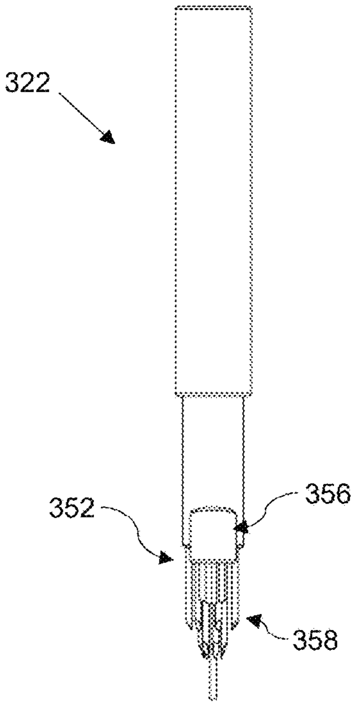
Figure 13B
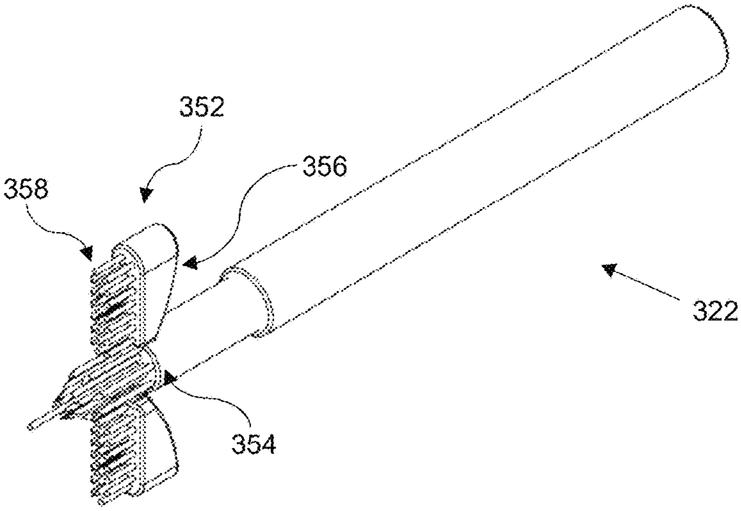
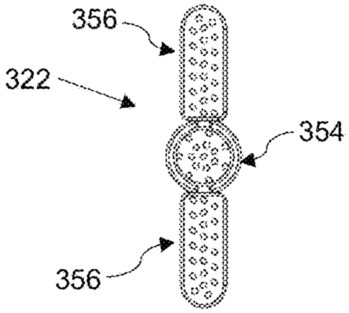
Figure 13C
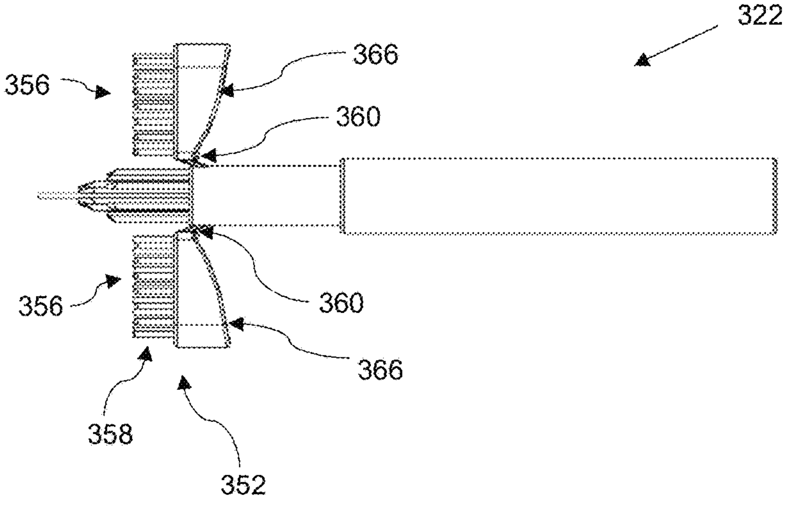
Figure 13D Figure 14A
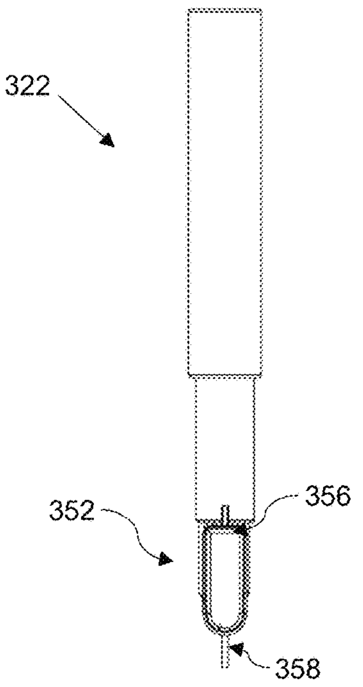
Figure 14B
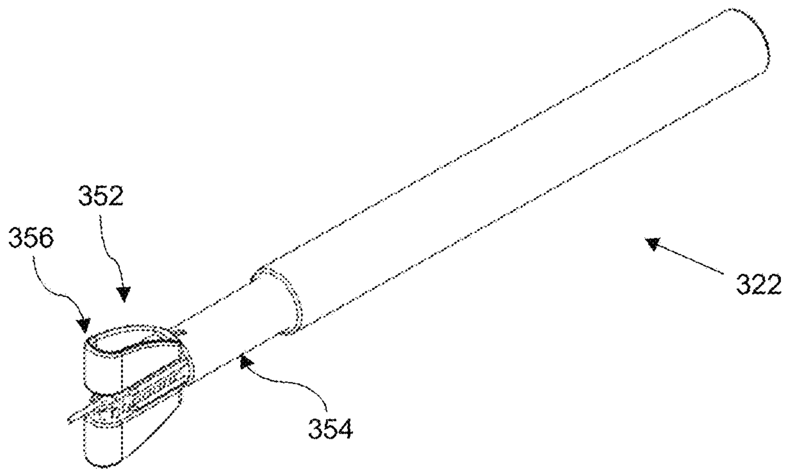
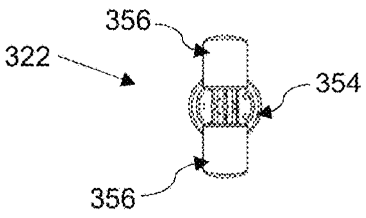
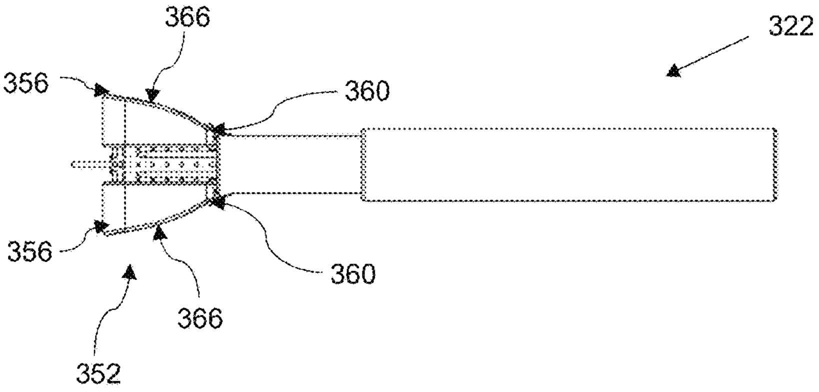
Figure 14C
Figure 14D Figure 15A
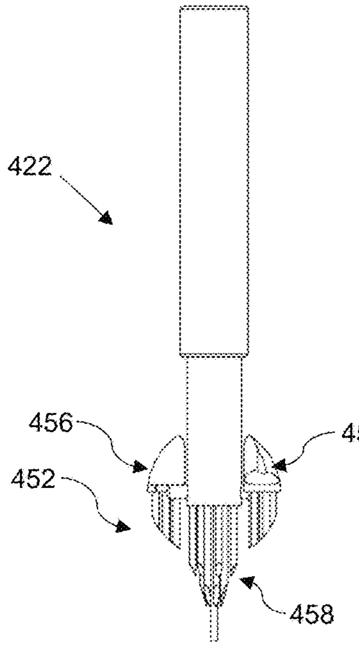
Figure 15B
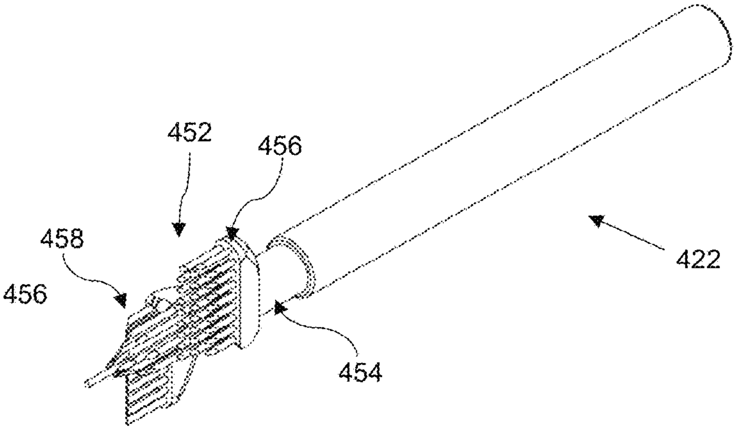
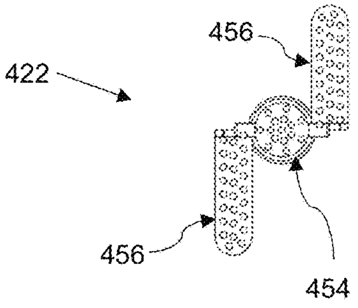
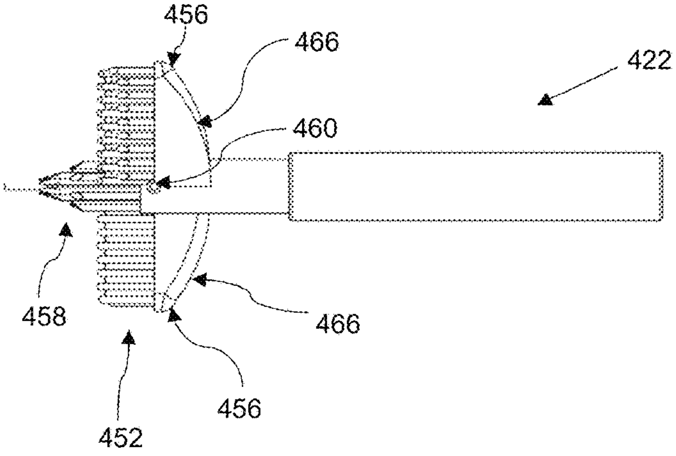
Figure 15C
Figure 15D Figure 17A
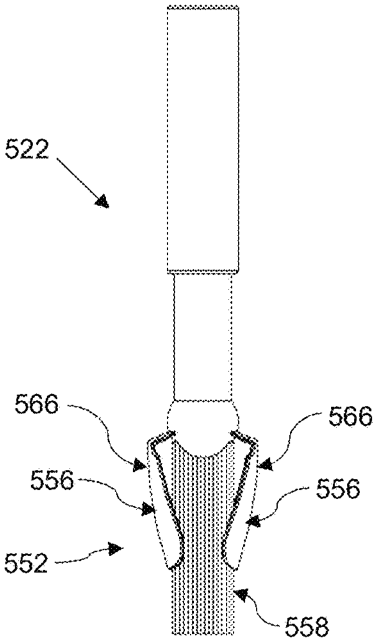
Figure 17B
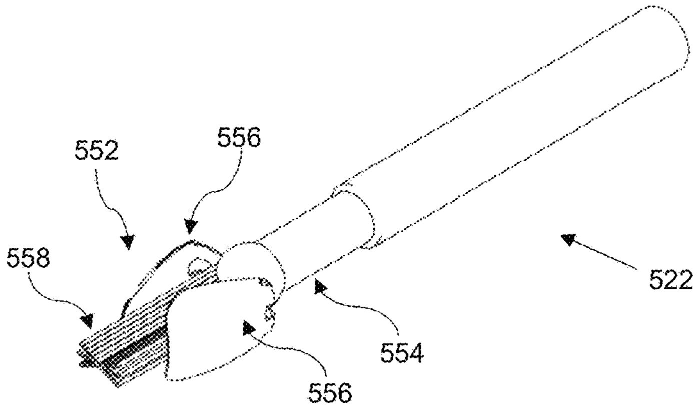
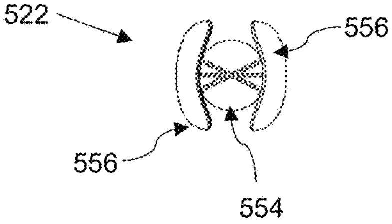
Figure 17C
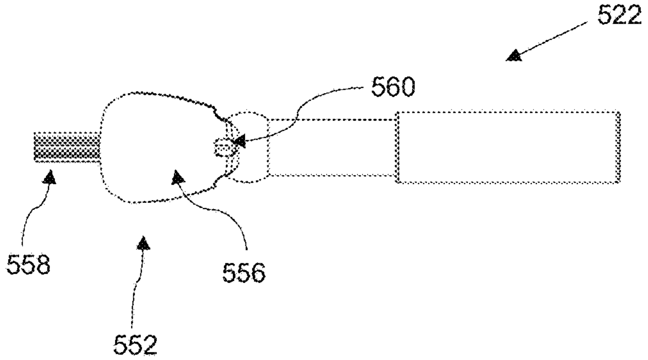
Figure 17D Figure 18A
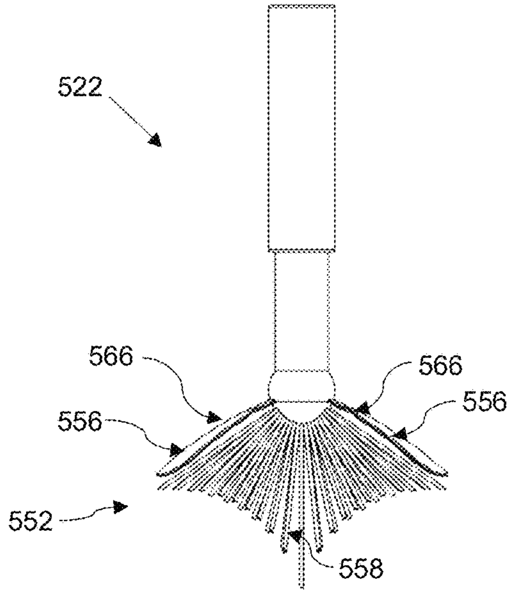
Figure 18B
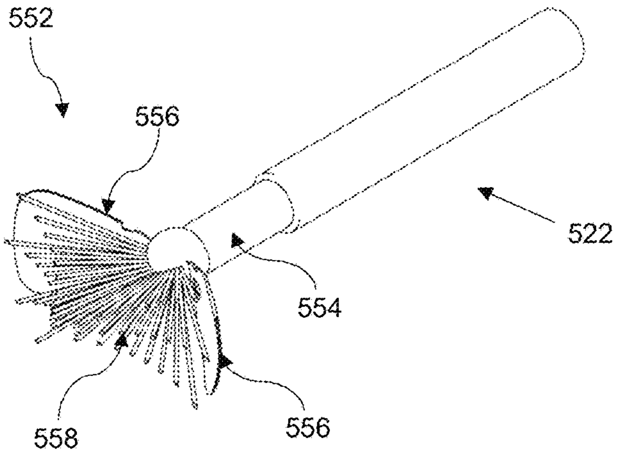
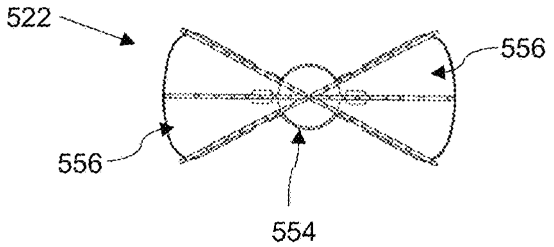
Figure 18C
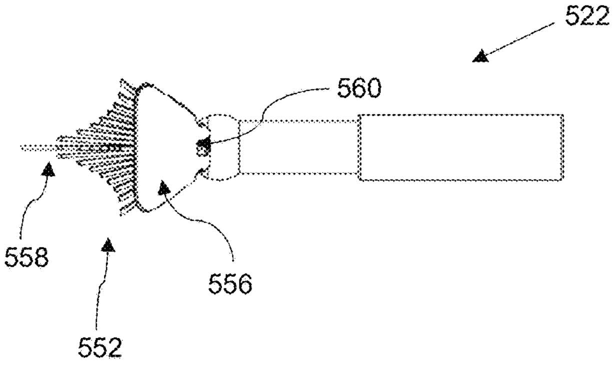
Figure 18D

CERVICAL INSPECTION DEVICE, METHODS OF CONTROL THEREOF, AND CERVICAL SAMPLING BRUSH

CROSS-REFERENCE TO RELATED APPLICATIONS

This application is a 35 U.S.C. 371 National Stage filing for PCT Application Ser. No. PCT/GB2022/052521, filed Oct. 6, 2022, which claims the priority benefit of GB Patent Application No. 2114384.7, filed on Oct. 7, 2021, the contents of each of which are herein incorporated by reference in their entireties.

The present invention relates to a cervical inspection device for facilitation of a cervical smear test. The invention also relates to a method of controlling a cervical inspection device for performing a cervical smear test. The invention further relates to a cervical sampling brush particularly but not exclusively for use in performing cervical smear tests.

Every woman over the age of twenty-five and a half is invited to a cervical smear screening test every three to five years. The intention is to collect a sample from the transformation zone of the cervix, which contains the squamocolumnar junction. This test collects cells from the transformation zone of the cervix to look for pre-cancerous changes. However, the transformation zone cannot be seen by the human eye, and the squamocolumnarjunction changes position with age. To obtain these cells a speculum is currently placed into the vagina and opened, which then allows the medical practitioner to visualise the cervix through the centre of the speculum. Once the cervix is visualised a collection device is inserted through the opened speculum and brushed over the cervix. The cells on the brush are then analysed for human papillomavirus (HPV) which if found is then analysed further for indications of cancer.

The brush commonly used in the UK is referred to as a Rovers (RTM) brush, which has a shaped head with flexible bristles adapted to the contours of the transformation zone of the cervix. This is an improvement over rigid spatulas and other less considerate endocervical devices. Rigid spatulas are also not compatible with the cytology solution used in the NHS in the UK. However, this brush is difficult to extract without loss of sample on extraction from the vagina, since touching the vaginal walls causes cross-contamination and potential loss of sample. In 2020, 40,000 samples were deemed inadequate. Lubrication can also cause contamination of samples, as can vaginal bleeding.

Furthermore, 1 in 4 women in the UK do not attend their cervical screenings. In 2020 this amounted to approximately 1.4 million women; in 2021 this had increased to 1.56 million. Embarrassment on body shape, pubic hair and shape of their vulva are considered to be contributing factors. Inability to get an appointment at a convenient time is another. Pain is also postulated as being a contributing factor and this is not readily acknowledged for fear it will put off women turning up for the test. When women do express pain and are unable to complete the test, they are often made to feel that they are the problem, rather than the discomfort of the test itself. However, this has significant consequences; it is estimated that 850 women die every year from cervical cancer, with a great percentage of these deaths being from non-white minority ethnic groups. Globally, the World Health Organization anticipates an annual increase in the number of new cases of cervical cancer to increase from 570,000 to 700,000 between 2018 and 2030, with anneal deaths increasing from 311,000 to 400,000. Improved testing rates would help to reverse this trend. Discomfort can be increased if a woman has a retroverted uterus, which occurs in around 1 in 5 patients. This means that instead of the uterus sitting forward over the bladder, it is directed backwards, or an alternative unorthodox position, over the rectum. If a woman has a retroverted uterus, when the smear test is performed whilst the patient is lain on her back, the cervix will not be linearly aligned to the vaginal canal. As such, a greater degree of force and movement of the speculum is required, which can cause pain, discomfort, and damage. The inability to use lubrication also increases the discomfort to the patient. Nulliparity, vaginismus, atrophy, and prior trauma are also possible reasons for painful examination, in addition to the selection of the incorrect size of speculum.

The present invention seeks to provide a means of performing a smear test accurately without the use of a speculum, as well as improving the ease with which the cervix can be located for the test.

According to a first aspect of the invention, there is provided a cervical sampling brush comprising: an elongate stem; and a cervical sampling head having a central hub and a lateral support, the cervical sampling head having a plurality of flexible sampling bristles thereon; wherein in a sampling condition, the lateral support has a first lateral extent relative to the elongate stem, and in a retraction condition, the lateral support is movable or foldable towards an axis of the elongate stem to adopt a second lateral extent which is less than the first lateral extent.

A speculum is an awkwardly-shaped device which can cause significant pain and discomfort to the patient. The size of the speculum is such that it can receive a standard cervical sampling brush therethrough. In the present invention, a cervical sampling brush is provided which has a reducible width in order to firstly be more comfortably receivable into the patient, since a smaller inspection device can be provided, and secondly, to provide an improved means of capture of the cervical smear sample on retraction. This latter point reduces the risk of loss of sample or contamination which would otherwise then require a repeat of the procedure.

Preferably, the lateral support may be engaged to the central hub via a hinge member.

A hinged engagement between the lateral support or supports and the central hub provides a simple means of folding of the lateral supports away, during the retraction procedure.

Optionally, the hinge member may be a resiliently flexible hinge.

If the cervical sampling head can be formed so as to use a resiliently flexible hinge, then the cervical sampling head can be biased towards the open position, so that no complex mechanisms are required to be operated once the cervical sampling brush is inserted into the vaginal canal. This reduces the likely discomfort for the patient.

Such a hinge axis for the lateral support may be parallel or substantially parallel with a longitudinal axis of the elongate stem.

Hinges which are present in parallel with the longitudinal axis allow for a furling and unfurling process to be achieved, gently opening the cervical sampling head. Even if there is pressure on the head from the cervix itself, this will not inhibit the sampling process, since the bristles will still remain accessible.

A pair of diametrically opposed lateral supports may be provided respectively connected to the central hub via opposed said hinge members, the lateral supports having rotationally symmetric arcuate shapes.

Rotationally symmetric lateral supports also allow for the furling and unfurling process described above, whilst also folding neatly up to the central hub without risk of pinching of the wall of the vaginal canal or cervix in the process.

Preferably, a pair of diametrically opposed lateral supports may be provided, respectively connected to the central hub via opposed said hinge members, wherein hinge axes of the hinge members are parallel to one another.

In a scenario in which the hinge members are parallel, and also preferably perpendicular to the primary axis of the cervical sampling brush, then the lateral supports act to trap the bristles during the extraction process, which may further serve to reduce the risk of cross-contamination or sample loss.

The lateral supports may be formed as linear supports. In an alternative embodiment, the lateral supports may be formed as fan-shaped supports.

Different shapes of cervical sampling head may yield different bristle configurations, which may be more appropriate for different cervical geometries, for example.

Optionally, a pair of diametrically opposed lateral supports may be provided, respectively connected to the central hub via opposed said hinge members, wherein hinge axes of the hinge members are co-axial. The lateral supports may be formed as linear supports.

The provision of co-axial hinges, typically formed using a single axle, may be the simplest mechanical means of providing the retraction motion, which may be more appropriate if a resiliently flexible hinge cannot provide the necessary range of motion.

Optionally, the or each lateral support may have a tapered bristle-distal edge to urge the or each lateral support into the retracted condition upon application of an axial force.

By providing an edge of each lateral support having a taper, the appropriate retraction movement into a cervical inspection device can be achieved, thus avoiding the need to provide any sort of actuator to change the configuration of the cervical sampling head inside the patient's vaginal canal.

According to a second aspect of the invention, there is provided a cervical inspection device for performing a cervical smear test, the device comprising: a tubular body having a first end which is engagable by an operator and a second end which is insertable into a patient's vaginal canal, the tubular body having a central bore which extends along its longitudinal axis for receiving a cervical sampling brush therethrough; and an expansion element at or adjacent to the second end of the tubular body; and control means operable from the first end of the tubular body for selectably expanding and/or contracting the expansion element; the expansion element forming a protective region beyond the central bore in an expanded condition thereof for the said cervical sampling brush to move through during a cervical smear test.

The provision of a cervical inspection device capable of protecting the path for the cervical sampling brush thereof all the way to the transformation zone of the cervix ensures that there is no cross-contamination of the sample. Providing an expansion element and mechanism for control thereof allows for the walls of the vaginal canal to be gently urged out of the way, ensuring that a good visual path is provided between the camera and the transformation zone, and also providing a suitable access route for the cervical sampling brush. It will also be appreciated that, since there is a central bore in the tubular body, this could also be utilised for other processes, such as introducing a sprayer device to spray the cervix with acetic acid, since this permits identification of the location of the transformation zone. Similarly, colposcopic tools could also be introduced in this manner.

The tubular body may comprise a brush housing which includes a channel forming the central bore.

If a dedicated unit is provided which forms the channel, this can be formed so as to be a housing for the cervical sampling brush once the sample is taken. This can further prevent contamination of the sample.

The brush housing may preferably be removable from the tubular body.

If the brush housing is completely removable, then the cervical sampling brush need never be exposed during the transfer process from sampling to cytology laboratory. This greatly reduces the risk of sample failure in transit.

Additionally, or alternatively, the tubular body may be a two-part body having a leading portion which is removable from a trailing portion.

In such an arrangement, the leading portion of the tubular body could be formed to be disposable, so that an operator of the device can swap between leading portions between patients, to minimise the risk of cross-contamination.

Preferably, there may be a camera receiving area at or adjacent to an end of the channel which is laterally spaced apart from the central bore and within a maximum lateral extent of the expansion element in the expanded condition. The camera receiving area may preferably have a window.

The location of a camera for the device is important. The point of any camera is to validate whether the tip of the brush enters the cervical opening, known as the internal cervical os, whilst the brush is in situ. As such, the camera needs to be present at the same time as the cervical sampling brush, but also not occluded by the protection region formed by the expansion element. The window of the brush housing provides a suitable barrier to prevent contamination of the camera lens, allowing the more complex parts of the cervical inspection device to be protected from the patient. This improves the between-patient sanitization process.

The cervical inspection device may further comprise a camera being positioned at or adjacent to second end of the tubular body so as to be laterally spaced apart from the central bore and within a maximum lateral extent of the expansion element in the expanded condition.

Having an in-built camera with the cervical inspection device greatly increases the utility of the device as a whole.

Preferably, the camera may be angled towards the central bore for monitoring the cervical sampling brush in use. There may also be an illumination element associated with the camera.

It is preferred that the camera be directed towards the expected target of the cervical sampling brush, to improve the accuracy of positioning of the cervical inspection device by the operator. Illumination can also assist with the identification of the correct cervical area.

Optionally, the expansion element may have a conical, frusto-conical, substantially conical, or substantially frusto-conical shape in the expanded condition.

A protection zone shaped in this manner provides ample room for manoeuvre of the cervical sampling brush, to ensure that the sample is extracted safely specifically from the transformation zone of the cervix.

A distal rim of the expansion element may in-use form a cervical-contact edge of the protection zone to form an enclosure with the cervix.

The expansion element could make direct physical contact with the cervix to thereby create a sealed region within which the cervical sampling brush can move without risk of contamination from, for example, the vaginal walls.

The expansion element may comprise a flexible hood, the control means comprising a plurality of tabs for urging the flexible hood into an open condition.

A flexible hood which can be operated outwardly is a gentle means of pushing the vaginal walls without risk of snagging or pinching on closure.

The cervical inspection device may further comprise a sheath which is receivable over the tubular body.

A sheath overlying the tubular body provides a suitably santizable and/or disposable outer layer for the cervical inspection device which can be replaced or cleaned following use. This protects the moving and delicate parts of the tubular body.

Preferably, the sheath may be connected to the brush housing.

If the sheath and brush housing are connected with one another, they can be removed as a unit, with the sheath providing additional protection for the sample enclosed within the brush housing on removal.

Optionally, an end of the sheath may form the flexible hood.

The outer layer of the sheath, being flexible, provides a suitable material for use as the flexible hood of the engagement element.

Preferably, the sheath may be formed from a silicone material.

Silicone is wipe-clean and easily disinfected, as well as providing a smooth outer surface for the cervical inspection device which will not cause pain to the patient on insertion.

In one embodiment, the control means may comprise a moveable member of the tubular body.

A moveable part of the tubular body itself, such as a sliding or driven cylinder, may be one simple mechanical means of providing a remote force at the second end of the cervical inspection device, suitable for controlling the expansion and contraction condition of the expansion element.

Preferably, the control means may engage with the expansion element in an interference fit to urge the expansion element into the expanded condition.

Wedging engagement is a natural means of creating radial expansion, which is desirable for the expansion characteristics of the expansion element.

The cervical inspection device preferably further comprises a cervical sampling brush comprising: an elongate stem; and a cervical sampling head having a central hub and a lateral support, the cervical sampling head having a plurality of flexible sampling bristles thereon; wherein in a sampling condition, the lateral support has a first lateral extent relative to the elongate stem, and in a retraction condition, the lateral support is movable or foldable towards an axis of the elongate stem to adopt a second lateral extent which is less than the first lateral extent, so as to be receivable into the tubular body without the plurality of flexible sampling bristles contacting the tubular body or the expansion element.

Optionally, the lateral support of the cervical sampling brush may be engaged to the central hub via a hinge member.

Preferably, the hinge member may be a resiliently flexible hinge.

Possible arrangements of the hinge member include: where a hinge axis for the lateral support is parallel or substantially parallel with a longitudinal axis of the elongate stem; or wherein a pair of diametrically opposed lateral supports is provided, respectively connected to the central hub via opposed said hinge members, wherein hinge axes of the hinge members are parallel to one another; or wherein a pair of diametrically opposed lateral supports is provided, respectively connected to the central hub via opposed said hinge members, wherein hinge axes of the hinge members are co-axial.

A pair of diametrically opposed lateral supports may be provided respectively connected to the central hub via opposed said hinge members, the lateral supports having rotationally symmetric arcuate shapes.

The lateral supports may be formed as linear or fan-shaped supports.

The or each lateral support may have a tapered bristle-distal edge to urge the or each lateral support into the retracted condition upon application of an axial force.

Optionally, the central bore may be at least in part dimensioned to receive the cervical sampling brush therethrough when the cervical sampling head is in the retracted condition.

The central bore of the cervical inspection device may be designed so that it naturally urges the cervical sampling brush into the retracted condition, eliminating the need for complex mechanisms for control of the sampling brush retraction conditions.

According to a third aspect of the invention, there is provided a method of controlling a cervical inspection device for performing a cervical smear test, the method comprising the steps of: providing a cervical inspection device in accordance with the second aspect of the invention, the expansion element being in a contracted condition; and using the control means, expanding the expansion element into the expanded condition to a protective region beyond the central bore through which a cervical sampling brush can pass.

According to a fourth aspect of the invention, there is provided a method of controlling a cervical inspection device for performing a cervical smear test, the method comprising the steps of: providing a cervical inspection device in accordance with the second aspect of the invention; pushing the cervical sampling brush through the central bore of the tubular body to permit opening of the cervical sampling head into the sampling condition; and pulling the cervical sampling brush into the central bore of the tubular body to urge the lateral supports of the cervical sampling brush to fold towards the central hub upon contact of the lateral supports with the tubular body.

Automatic closure of the cervical sampling brush on retraction provides a simple means of using a cervical inspection device which obviates the need for a speculum, without needing to prepare complex moving parts.

According to a fifth aspect of the invention, there is provided a cervical inspection device for performing a cervical smear test, the device comprising: a tubular body having a first end which is engagable by an operator and a second end which is insertable into a patient's vaginal canal; a sheath receivable over the tubular body; and a cervical inspection tool housing receivably engagable with the tubular body to form an inner barrier to the tubular body, the cervical inspection tool housing having a central bore which extends along a longitudinal axis thereof for receiving a cervical inspection tool therethrough.

The ability to dispose of the patient-contact portions of a cervical inspection device following use, in the form of internal and external barrier sheaths, allows for rapid sanitization not easily conducted with a speculum.

Preferably, the sheath may be connected to the cervical inspection tool housing.

Optionally, an end of the sheath may form a flexible hood of an expansion element of the cervical inspection device.

In a preferred embodiment, the flexible hood may form a barrier for internal and external surfaces of the expansion element.

Preferably, the sheath may have an opening at an end thereof to permit a cervical inspection tool to pass therethrough.

Optionally, the cervical inspection device may have a camera positioned at or adjacent to the second end of the device.

According to a sixth aspect of the invention, there is provided a sheath for use with a cervical inspection device preferably in accordance with the second or fifth aspects of the invention, the sheath comprising: an at least in part flexible body; a first opening at a first end of the body for receivably engaging over a said cervical inspection device, and a second opening at a second end of the body to permit a cervical inspection tool to pass therethrough.

A disposable sheath which can overlie a tubular body of the cervical inspection device is useful to protect the more complex components of the cervical inspection device from contact with the vaginal canal. This prevents or significantly reduces cross-contamination between patients.

Preferably, the sheath further comprises a cervical inspection tool housing to form an inner barrier for said cervical inspection device, the cervical inspection tool housing having a central bore which extends along a longitudinal axis thereof for receiving a cervical inspection tool therethrough.

According to a seventh aspect of the invention, there is provided a cervical inspection device for performing a cervical smear test, the device comprising: a tubular body having a first end which is engagable by an operator and a second end which is insertable into a patient's vaginal canal, the tubular body having a central bore which extends along its longitudinal axis for receiving a cervical inspection tool therethrough; an expansion element at or adjacent to the second end of the tubular body; control means operable from the first end of the tubular body for selectably expanding and/or contracting the expansion element; and a camera at or adjacent to second end of the tubular body so as to be laterally spaced apart from the central bore and within a maximum lateral extent of the expansion element in the expanded condition.

By combining the features of a camera and an expansion element which can be activated internally within the patient, the need for a speculum, and thus the discomfort which accompany such a device, can be eliminated.

The invention will now be more particularly described, by way of example only, with reference to the accompanying drawings, in which:

FIG. 5A shows a perspective representation of the device body of the cervical inspection device of FIG. 4 in a retracted condition;

FIG. 5B shows the device body of FIG. 5A in an inspection condition;

FIG. 13A shows a plan view of a second embodiment of cervical sampling brush in accordance with the first aspect of the invention, in an extended state;

FIG. 13B shows a perspective view of the cervical sampling brush of FIG. 13A;

FIG. 13C shows an end view of the cervical sampling brush of FIG. 13A;

FIG. 13D shows a side view of the cervical sampling brush of FIG. 13A;

FIG. 14A shows a plan view of the cervical sampling brush of FIG. 13A, in a retracted state;

FIG. 14B shows a perspective view of the cervical sampling brush of FIG. 14A;

FIG. 14C shows an end view of the cervical sampling brush of FIG. 14A;

FIG. 14D shows a side view of the cervical sampling brush of FIG. 14A;

FIG. 15A shows a plan view of a third embodiment of cervical sampling brush in accordance with the first aspect of the invention, in an extended state;

FIG. 15B shows a perspective view of the cervical sampling brush of FIG. 15A;

FIG. 15C shows an end view of the cervical sampling brush of FIG. 15A;

FIG. 15D shows a side view of the cervical sampling brush of FIG. 15A;

FIG. 17A shows a plan view of a fourth embodiment of cervical sampling brush in accordance with the first aspect of the invention, in a retracted state;

FIG. 17B shows a perspective view of the cervical sampling brush of FIG. 17A;

FIG. 17C shows an end view of the cervical sampling brush of FIG. 17A;

FIG. 17D shows a side view of the cervical sampling brush of FIG. 17A;

FIG. 18A shows a plan view of the cervical sampling brush of FIG. 17A, in an extended state;

FIG. 18B shows a perspective view of the cervical sampling brush of FIG. 18A;

FIG. 18C shows an end view of the cervical sampling brush of FIG. 18A;

FIG. 18D shows a side view of the cervical sampling brush of FIG. 18A;

Figure 1:
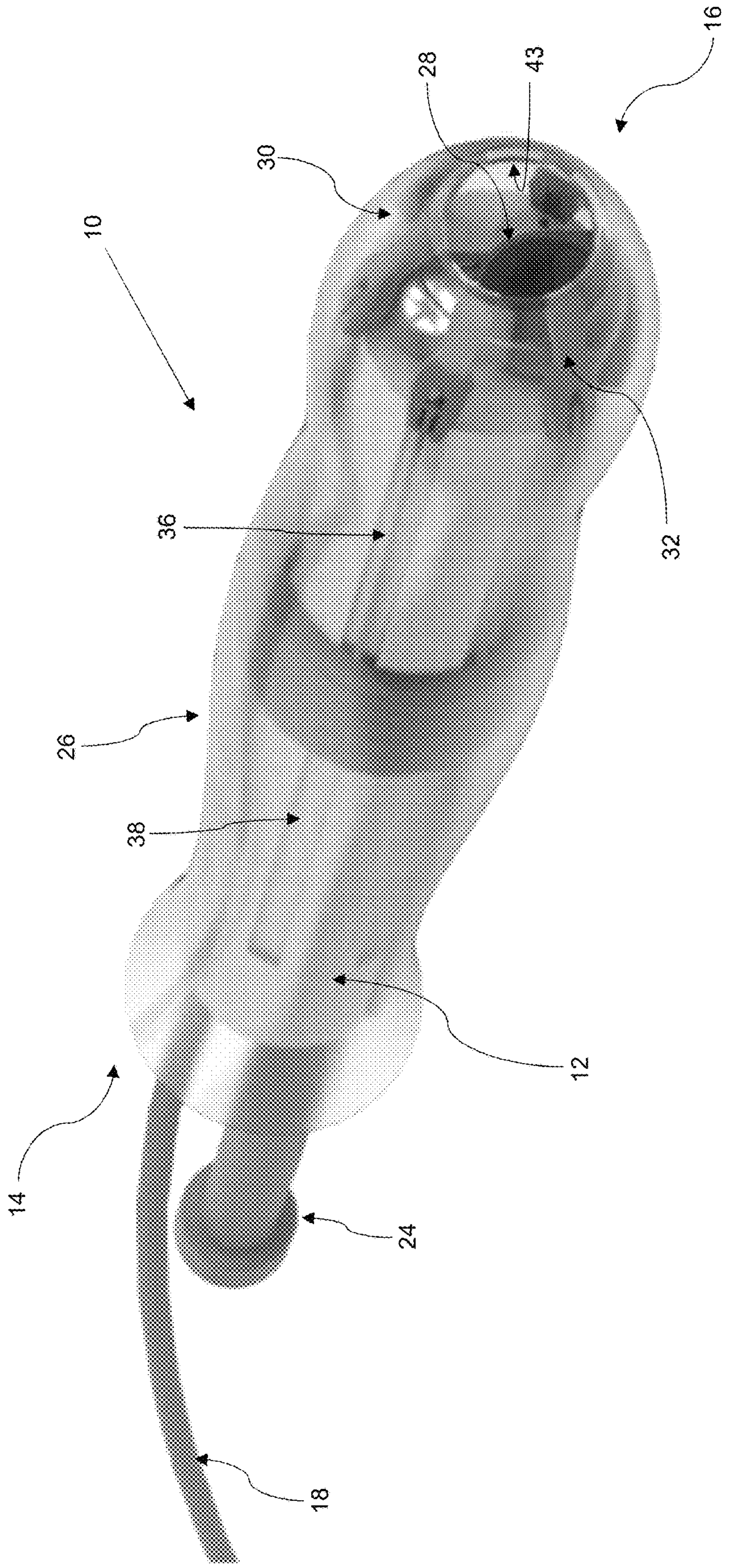
FIG. 1 shows a perspective representation of a first embodiment of a cervical inspection device in accordance with the second aspect of the invention for performing a cervical smear test.

Referring to FIG. 1, there is indicated a cervical inspection device, referenced globally at 10, which is adapted for performing a cervical smear test, in a manner which also permits inspection of the transformation zone of the cervix in use.

The cervical inspection device 10 has a tubular body 12 which has a first end 14 which is engagable by an operator, typically a nurse, and a second end 16 which is insertable into the patient's vaginal canal. A power cable 18 can be seen extending through the first end 14 to provide a power supply to the electronic components of the apparatus. It will be apparent that the power cable 18 could also be used as the conduit for information transfer to and from the device 10, such as a video feed, and that this could additionally or alternatively be performed wirelessly.

Figure 2:
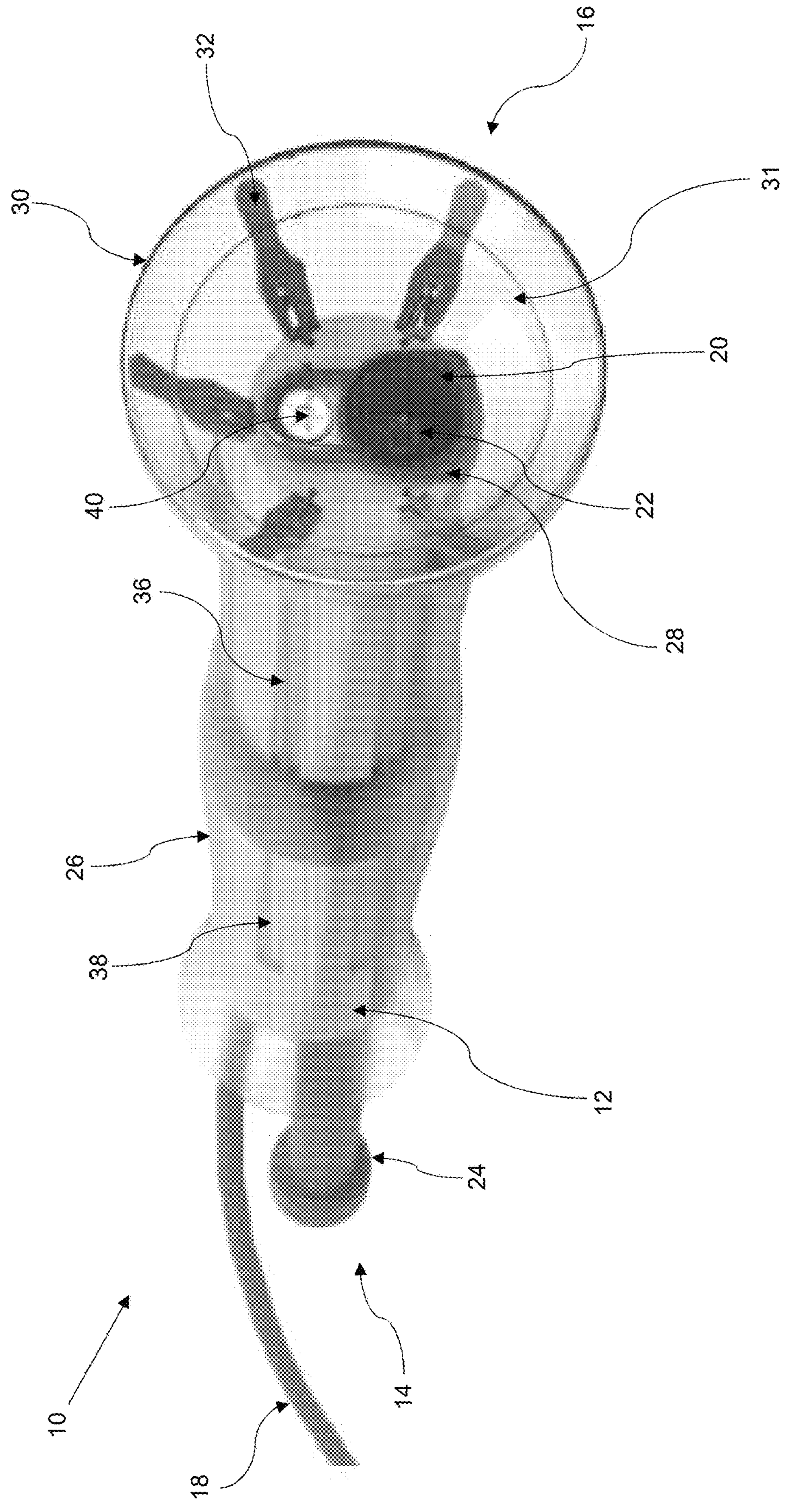
FIG. 2 shows a perspective representation of the cervical inspection device of FIG. 1 in an inspection condition.

The tubular body 12 has a central bore 20 which extends along a longitudinal axis thereof, and this is best seen in FIG. 2. A cervical sampling brush 22 can be seen housed inside the central bore 20 in a retracted state in FIG. 2, the brush 22 being linearly advanced using a manually operable handle 24. The central bore 20 is designed to be dimensioned to receive the cervical sampling brush 22 therein when the cervical sampling brush 22 is in a retracted state. This will be discussed in more detail below.

The cervical inspection device 10 is here provided with a sheath 26 receivable over the tubular body 12. This provides a smooth insertion surface to prevent snagging on the walls of the vaginal canal. The sheath 26 may preferably be formed from a silicone material, or similarly disinfectable, sterilisable, or wipe-clean material. Disposable materials could also be considered, such as a paper sheath. The sheath 26 is shown removed from the tubular body 12 in FIG. 3. It will be apparent, however, that a sheath could be dispensed with.

The sheath 26 may be preferably connected to a, preferably disposable, brush housing 28 receivable into the tubular body 12 which forms the central bore 20. Alternatively, the main tubular body could form the brush housing directly. The brush housing 28, which may be a rigid unit, provides a physical barrier between the patient and the tubular body 12, which prevents contamination of the cervical inspection device 10 between patients. The brush housing 28 may therefore slot into a corresponding channel 29 formed in the tubular housing 12. The sheath 26 and brush housing 28 thus together form a complete barrier layer for the tubular housing 12, thereby allowing it to be inserted into a patient's vaginal canal without risk of contamination. The sheath 26 and brush housing 28 thus may be provided as a disposable unit, comprising external and internal barriers for the tubular housing 12 respectively.

This brush housing 28 can also act as a transferrable housing for the cervical sampling brush 22 to a cytological analysis laboratory, where this process is used, reducing the risk of cross-contamination. It will be apparent that the brush housing 28, where provided, need not necessarily be connected to the sheath 26; this is merely an advantageous feature which allows to two components to be safely removed from the tubular body 12 as one for sample transfer. In the depicted embodiment, however, the sheath 26 covers the end of the tubular housing 12 not otherwise covered by the brush housing 28, thereby completing the barrier between the patient and the tubular housing 12. This configuration allows the sheath 26 to have an open end through which the brush 22 can penetrate.

It is preferred that the cervical inspection device 10 include an expansion element 30 which is openable to allow for improved inspection capability and protection at the transformation zone of the cervix, since such an expansion element 30 can push the walls of the vaginal canal out for improved visuals and to allow the brush to unfurl in an unhindered manner. The expansion element 30 also forms a protection region around the transformation zone, preferably but not necessarily engaging with the cervix directly in use at a cervix-contact edge thereof, so that the brush can be safely advanced therethrough so that it only contacts the transformation zone and is not contaminated, for example, by the vaginal walls of the patient. The expansion element 30 could of course stop short of contacting the cervix, whilst still also creating or substantially creating a protection region.

Figure 3:
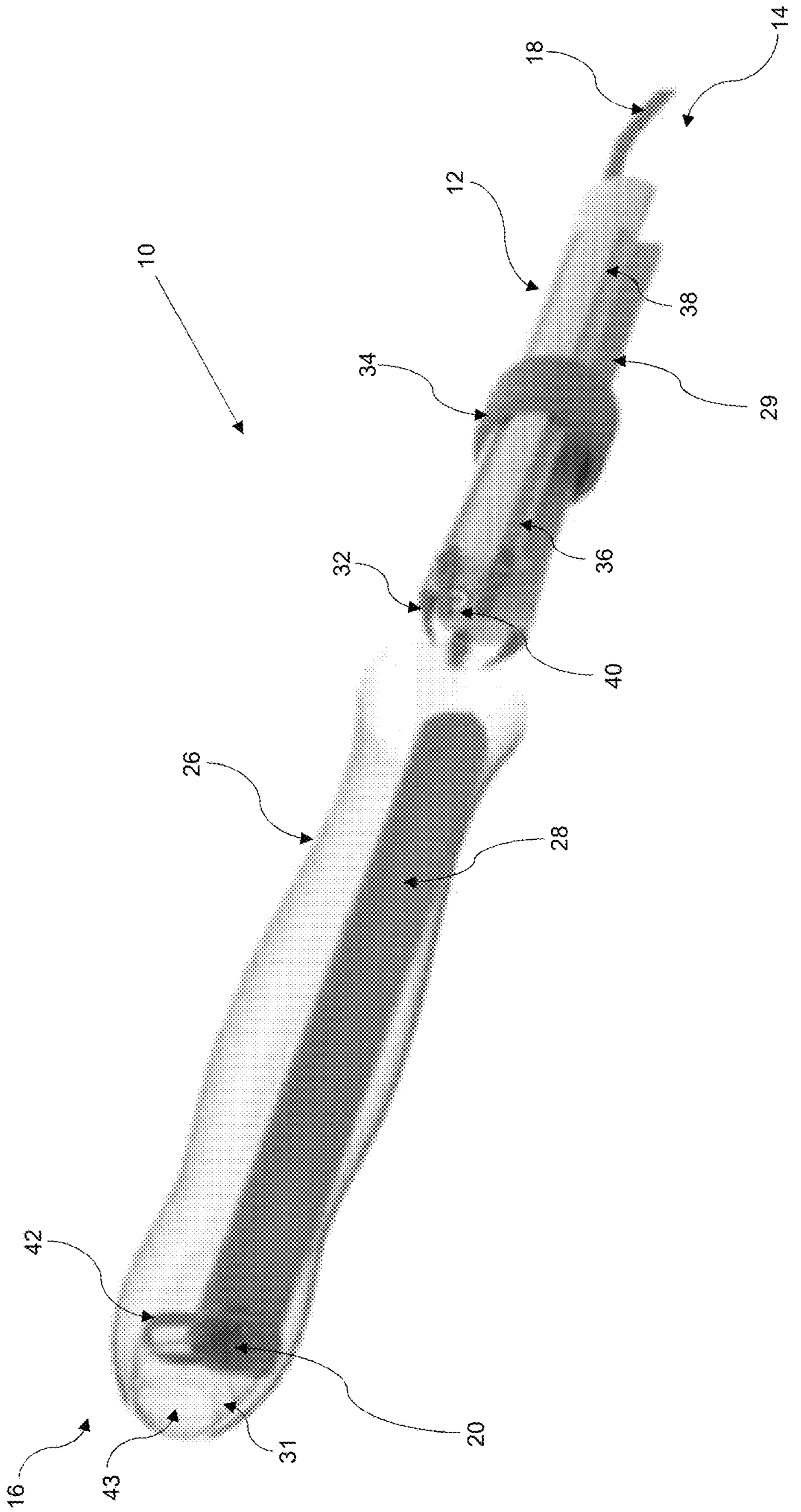
FIG. 3 shows an exploded perspective representation of the cervical inspection device of FIG. 1.

In the illustrated embodiment of FIGS. 1 to 3, the expansion element 30 is provided as a flexible hood 31 of the sheath 26, operated by a control means. The control means comprises a plurality of tabs 32 which are arranged to urge the expansion element 30 between the closed and open positions respectively shown in FIGS. 1 and 2. The flexible hood 31 covers the inside and outside surfaces of the tabs 32, so that they are occluded from the vaginal canal in use. The flexible hood 31 can thus connect to the outer edge of the brush housing 28 in order to form a continuous barrier protecting the tubular housing 28.

The tabs 32 may be hingeably connected to the second end 16 of the tubular body 12, being pivotable by a linear slider 34 which is positioned on the outside of the tubular body 12, typically under the sheath 26. Pushing the slider 34 towards the second end 16 will effectively push the tabs 32 into the closed condition based on the relative connection points of the pivot points with respect to a wire connection 36 between the slider 34 and the tabs 32. Pulling the slider 34 pulls on the wire connections 36 pulling the tabs 32 outwards, and opening the expansion element 30. The tubular body 12 may optionally have runners 38 within which the wire connections 36 are moveable, extending parallel to the longitudinal axis.

Whilst the sheath 26 in the depicted embodiment provides the flexible hood of the expansion element 30, it will be apparent that the expansion element could be formed as a unitary component, without the need to provide a separate sheath. The expansion element would thereby form the protection region by itself.

Whilst a slider-and-wire arrangement is shown, there could equally be provided a moveable member within the tubular body 12 which controls the expansion and/or contraction function of the expansion element 30. For example, a movable cylinder within the tubular body could be provided, which at least in part forms the central bore, and a distal end of such a cylinder could be formed so as to create an interference fit with the base of the expansion element. This cylinder would then urge against the tabs, or similar tines or members of the expansion element, to splay them outward and create a protection region. Such tabs, tines or members could be hinged to the tubular body, or could be at least in part flexible, for example. Advantageously, since the splaying of the expansion element 30 occurs at or adjacent to the second end 16 of the cervical inspection device 10, there is no increase in dimension of the tubular body 12 within the vagina, which would otherwise cause pain to the patient.

The use of the expansion element 30 to improve visual access to the transformation zone is useful since the cervical inspection device 10 includes a camera 40 at or adjacent to the second end 16. This may be protected via a camera receiving area, here illustrated as a camera window 42, which may be formed as a transparent or translucent cover on the brush housing 28. Preferably, there will also be an illumination element, such as an LED, associated with the camera 40 to ensure that visual inspection is feasible. A video feed may be transmitted via the same cable as the power cable 18. An aperture 43 forming the open end of the sheath 26 allows for the camera 40 to have a viewing field including the cervix on entry, in addition to providing access for the brush 22. The aperture 43 provides an unobscured visual path for the camera 40 even when the expansion element 30 is in the closed condition.

The camera 40 is preferably positioned laterally or radially outwardly of the central bore 20, so as not to obstruct the cervical sampling brush 22 in use. To this end, the camera 40 is preferably angled towards the central bore 20 so as to be able to monitor the movements of the cervical sampling brush 22 in use. Crucially, the camera 40 is positioned in such a manner as to be able to inspect inside the protection region, that is, the region created about the cervix in-use by the expansion element 30. Whilst the camera 40 is thus spaced apart from the central bore 20, it does remain within the lateral or radial extent of the distal end of the expansion element 30, when in the expanded condition.

Figure 4:
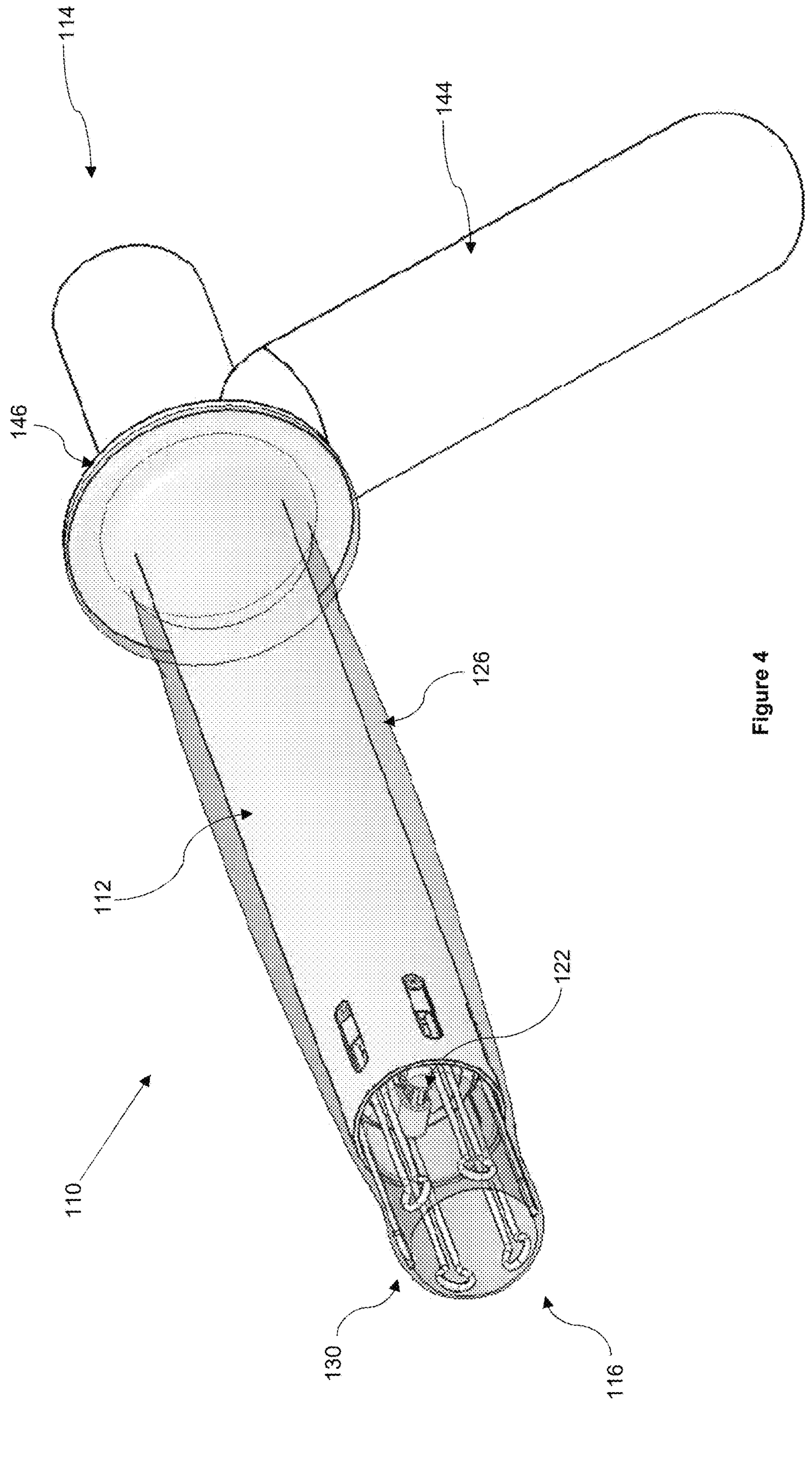
FIG. 4 shows a perspective representation of a second embodiment of a cervical inspection device in accordance with the second aspect of the invention for performing a cervical smear test, the device including a cervical sampling brush in accordance with the first aspect of the invention.

An alternative embodiment of cervical inspection device 110 is shown in FIG. 4, embodying many of the same principles as the first embodiment. As such, identical or similar features of the first embodiment will be referenced using identical or similar reference numerals, and further detailed description will be omitted for brevity.

The cervical inspection device 110 is shown with an extended handle 144, which allows the user greater control over the whole device 110. A flange 146 is provided towards the first end 114 of the tubular body 112 in order to improve grip. It is not intended as a means of identifying an insertion depth of the device 110, since the device 110 is usable for all patients, which is a significant improvement over speculums having different dimensions.

The external slider is absent from the indicated embodiment; instead, the tabs 132, which are here formed as bent wire formations, are operated via movement of the tubular housing 112 itself. The range of movement of the tabs 132 can be seen in detail in FIGS. 5A and 5B. The brush housing 128 of the cervical inspection device 110 is adapted to be fixed relative to the tabs 132. The tabs 132 are provided so as to be outwardly biased, for example, by a spring member, which urges them into the open condition. When the tubular housing 112 is in a forward position towards the second end 116 of the device, as shown in FIG. 5A, pins 147 are held captive towards a rear end of runners 138. The tabs 132 are held in position within the end of the tubular body 112 by compression of the tabs 132 towards one another by the internal surface of the tubular body 112. As the tubular body 112 is urged backwards, the pins 147 become positioned relatively forward within runners 138, until a spring force of the tabs 132 overcomes the compression thereof, and the tabs 132 become splayed relative to one another.

Figure 6:
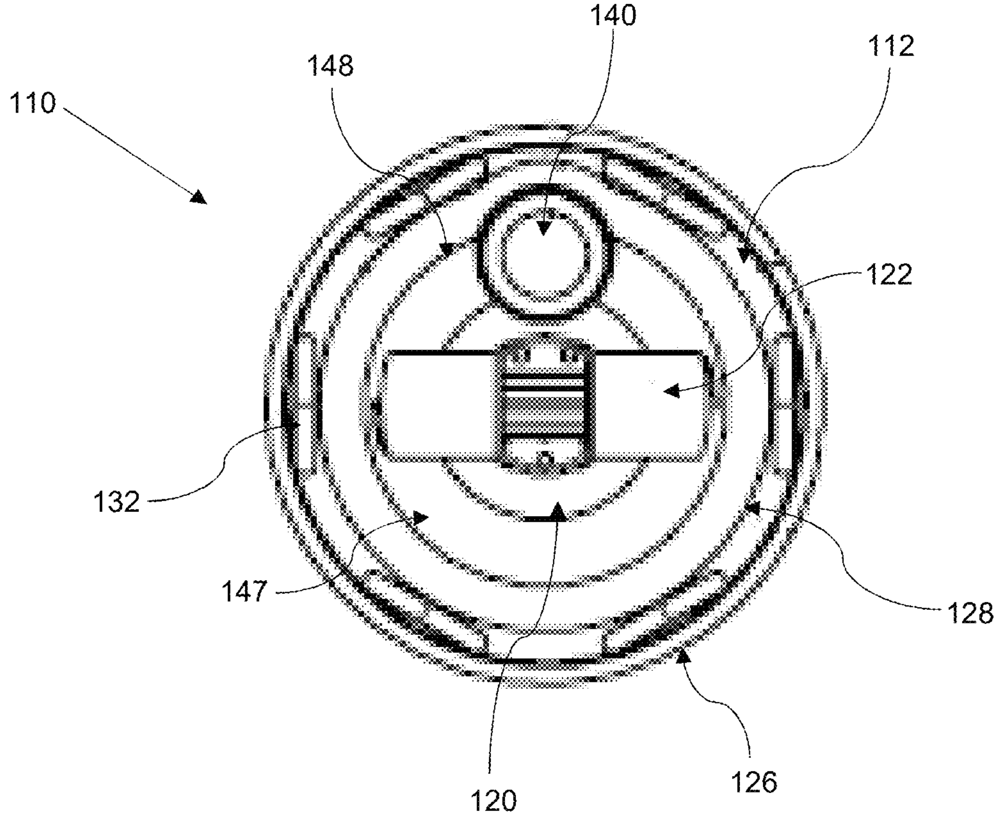
FIG. 6 shows an end view of the cervical inspection device of FIG. 4.
Figure 7:
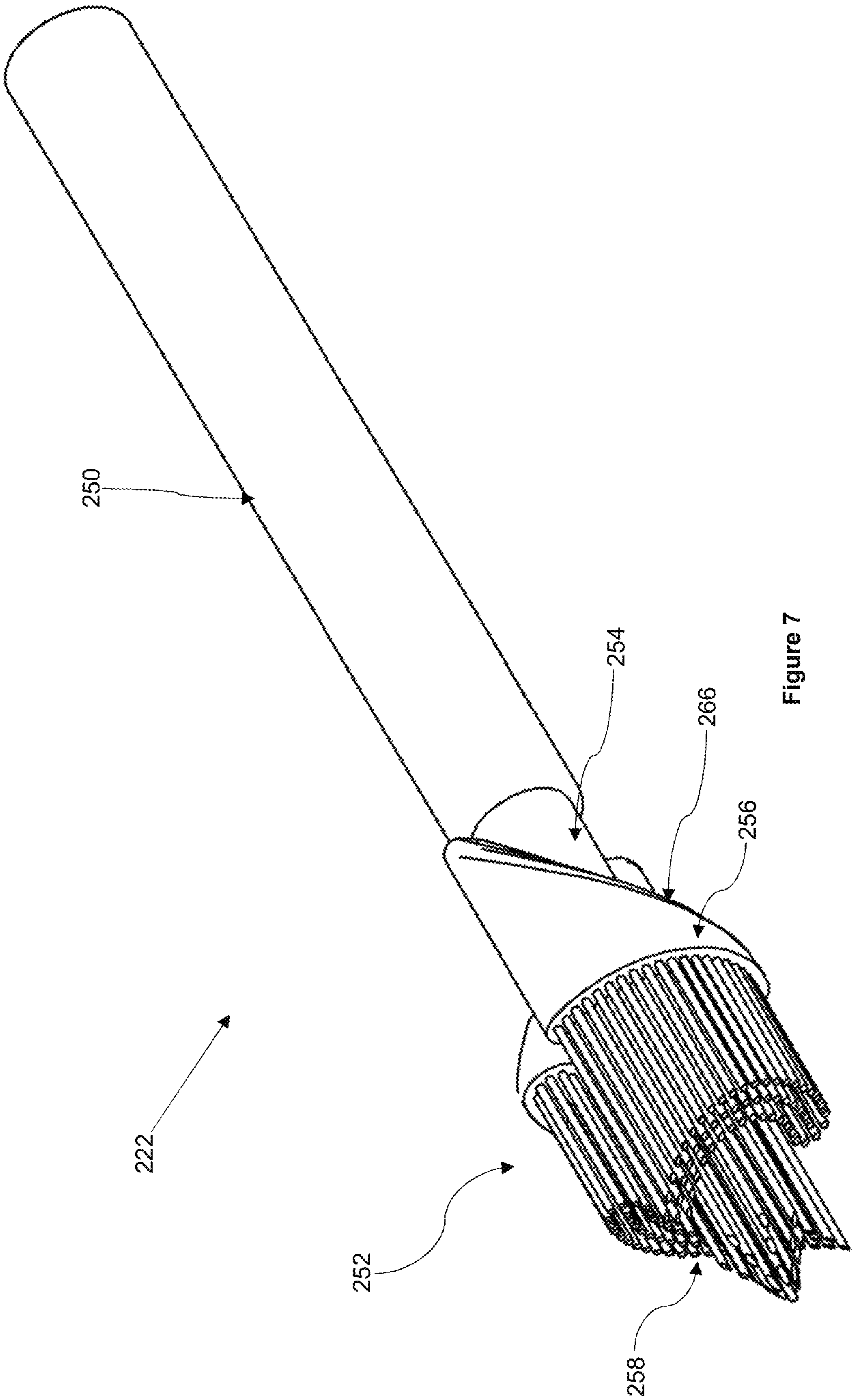
FIG. 7 shows a perspective representation of a first embodiment of a cervical sampling brush in accordance with the first aspect of the invention, in a closed condition.
Figure 8:
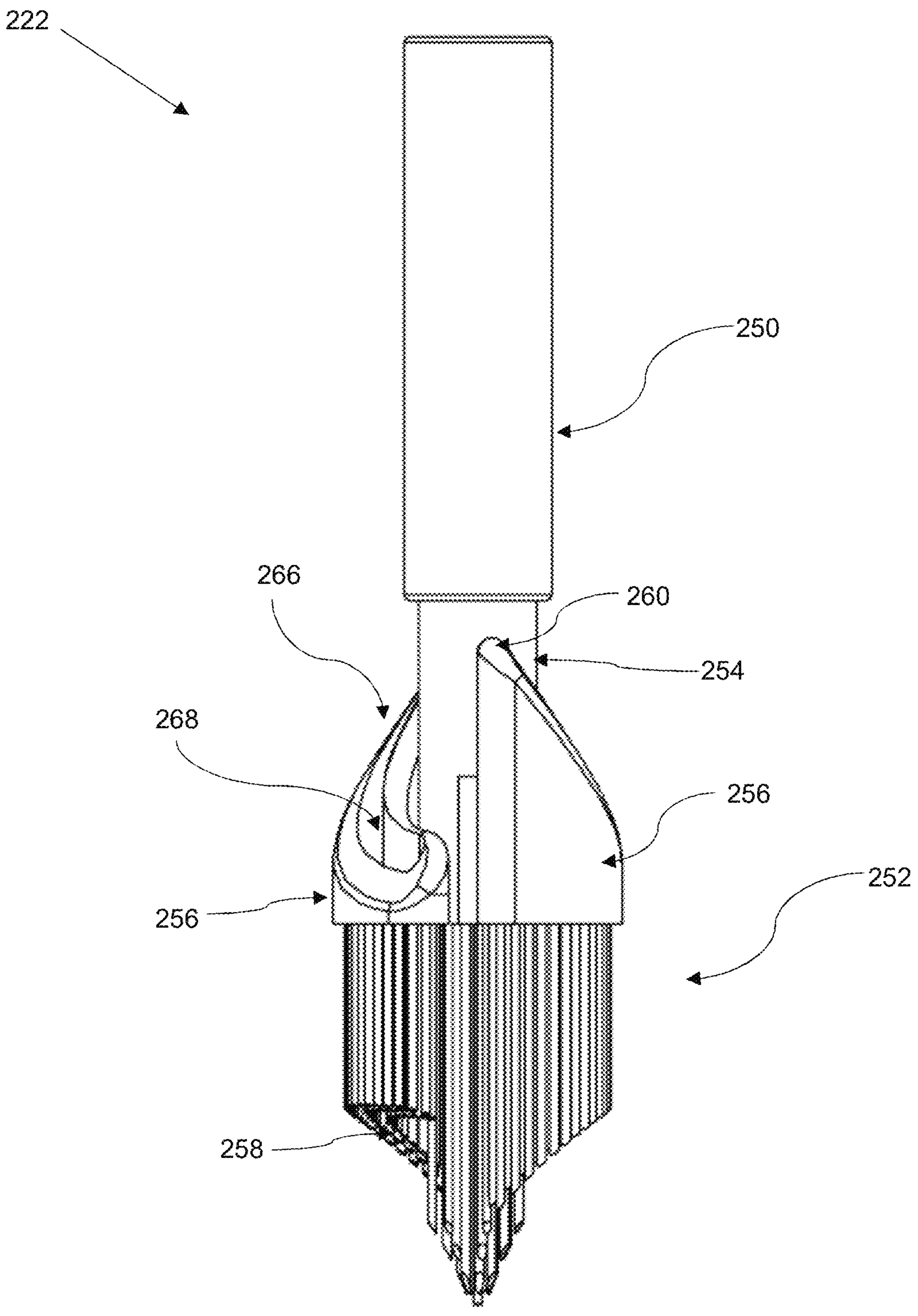
FIG. 8 shows a plan view of the cervical sampling brush of FIG. 7.
Figure 9:
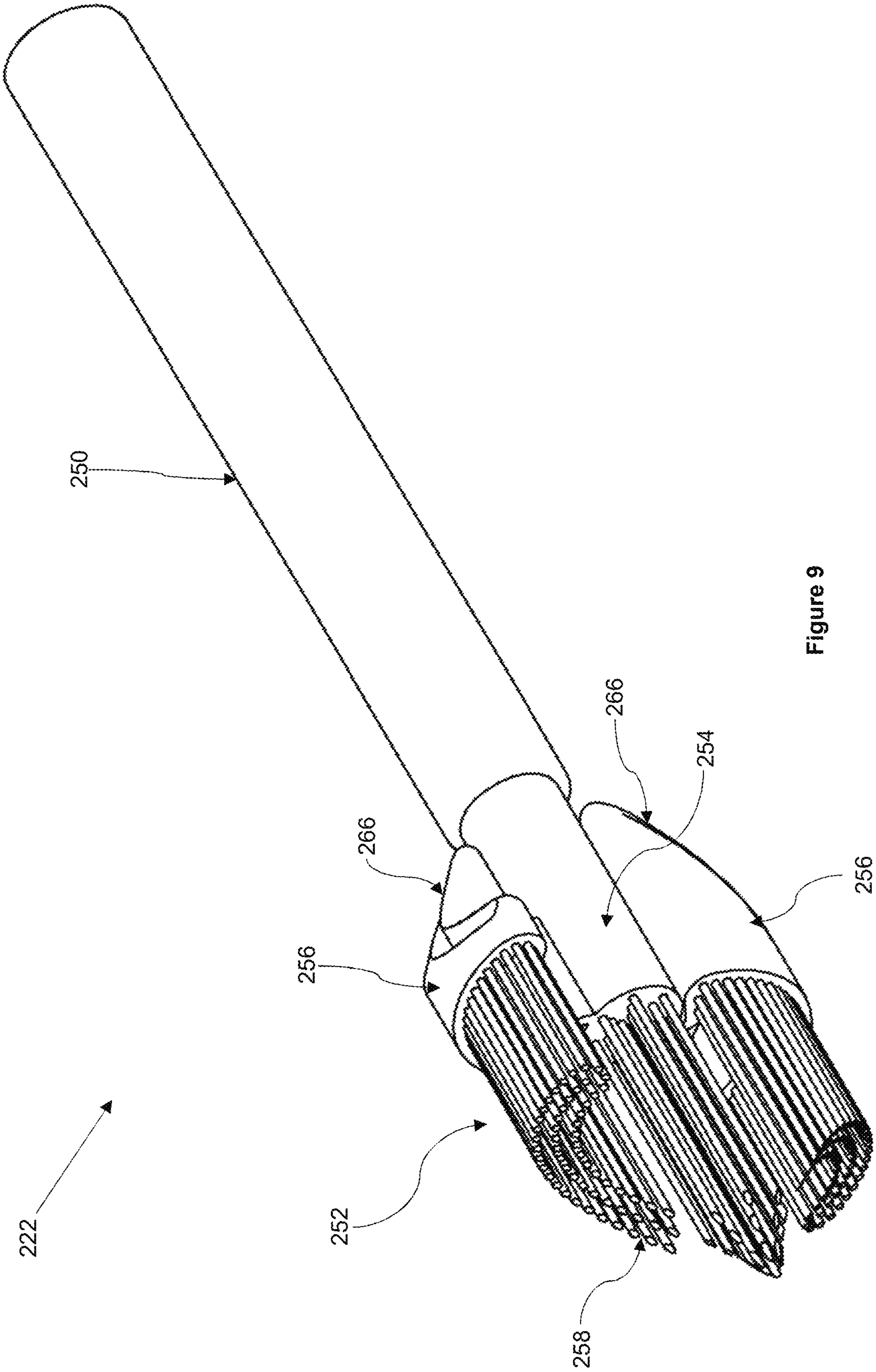
FIG. 9 shows a perspective representation of the cervical sampling brush of FIG. 7, in a sampling condition.
Figure 10:
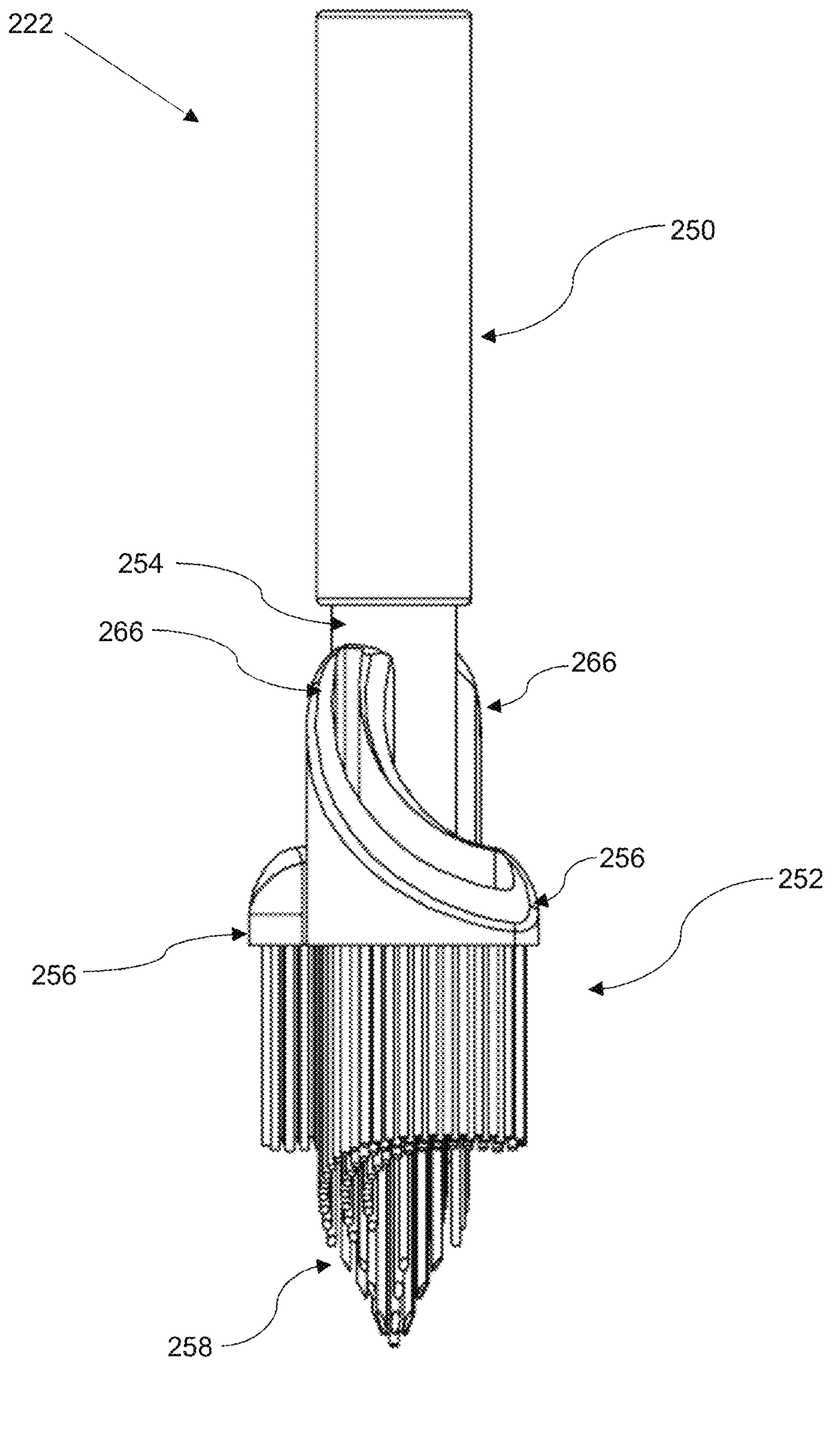
FIG. 10 shows a plan view of the cervical sampling brush of FIG. 9.

FIG. 6 shows the dimensions of the brush housing 128 in detail, since the cervical inspection device 110 is viewed end on. The central bore 120 is formed as a cylindrical void, and the cervical sampling brush 122 is adapted to fold or retract into a condition which is receivable within the central bore 120 fully, with the central bore 120 most preferably being dimensioned such that the cervical sampling brush 122 can be moved through the central bore 120. However, the brush housing 128 may, as illustrated, having an internal stop 147 which inhibits full removal of the brush 122 from the brush housing 128, such that it can only be removed or loaded from the second end 116. The folding or retraction means may be initiated or urged through contact with an outer rim 148 of the central bore 120 of the brush housing 128, or indeed any structure which forms or comprises part of the central bore 120. Alternatively, the cervical sampling brush could itself be provided with an actuation mechanism to cause folding. Crucially, the folding is such that the bristles of the brush 122 do not contact the walls of the brush housing 128, as will be described in more detail below.

The structure of an indicative, and indeed presently preferred, embodiment of cervical sampling brush 222 is illustrated in FIGS. 7 to 11D. FIGS. 7, 8, 11A, and 11B show the cervical sampling brush 222 in a closed or retracted condition or state, and FIGS. 9, 10, 11C, and 11D show the cervical sampling brush 222 in an open or sampling condition or state.

The cervical sampling brush 222 has an elongate stem 250, which here is indicated as a generalised cylindrical handle, and is not necessarily depicted to scale. At one end of the elongate stem 250 is a cervical sampling head 252 which has a central hub 254 and a pair of lateral supports 256. The pair of lateral supports 256 are preferably diametrically opposed to one another for uniformity of movement. It is noted that a single lateral support could be considered, if this makes the folding process more straightforward, but having paired lateral supports 256 allows for a better matching of the shape of the cervical wall in the transformation zone.

The cervical sampling head 252 has a plurality of flexible sampling bristles 258 thereon, which are preferably designed for best capture properties of a cervical sample. This will typically involve longer bristles 258 at the central hub 254, which gradually become shorter towards the lateral edges of the lateral supports 256.

The lateral supports 256 have, in the open condition, a first lateral extent, which could be characterised as a radial extent, and a second lateral extent, in the closed condition, which is less than the first lateral extent. This is achieved by folding or moving of the lateral supports 256 towards the central hub 254.

The lateral supports 256 are preferably integrally formed with the central hub 254, being connected by a hinge member 260, which may preferably be a resiliently flexible hinge. This can be best visualised in FIGS. 11A and 11C which show the open and closed conditions of the lateral supports 256 most clearly. In this instance, a hinge axis of the hinge members 260 is parallel with or substantially parallel with the longitudinal axis of the cervical sampling brush 222.

Figures 11A, 11B, 11C, 11D:
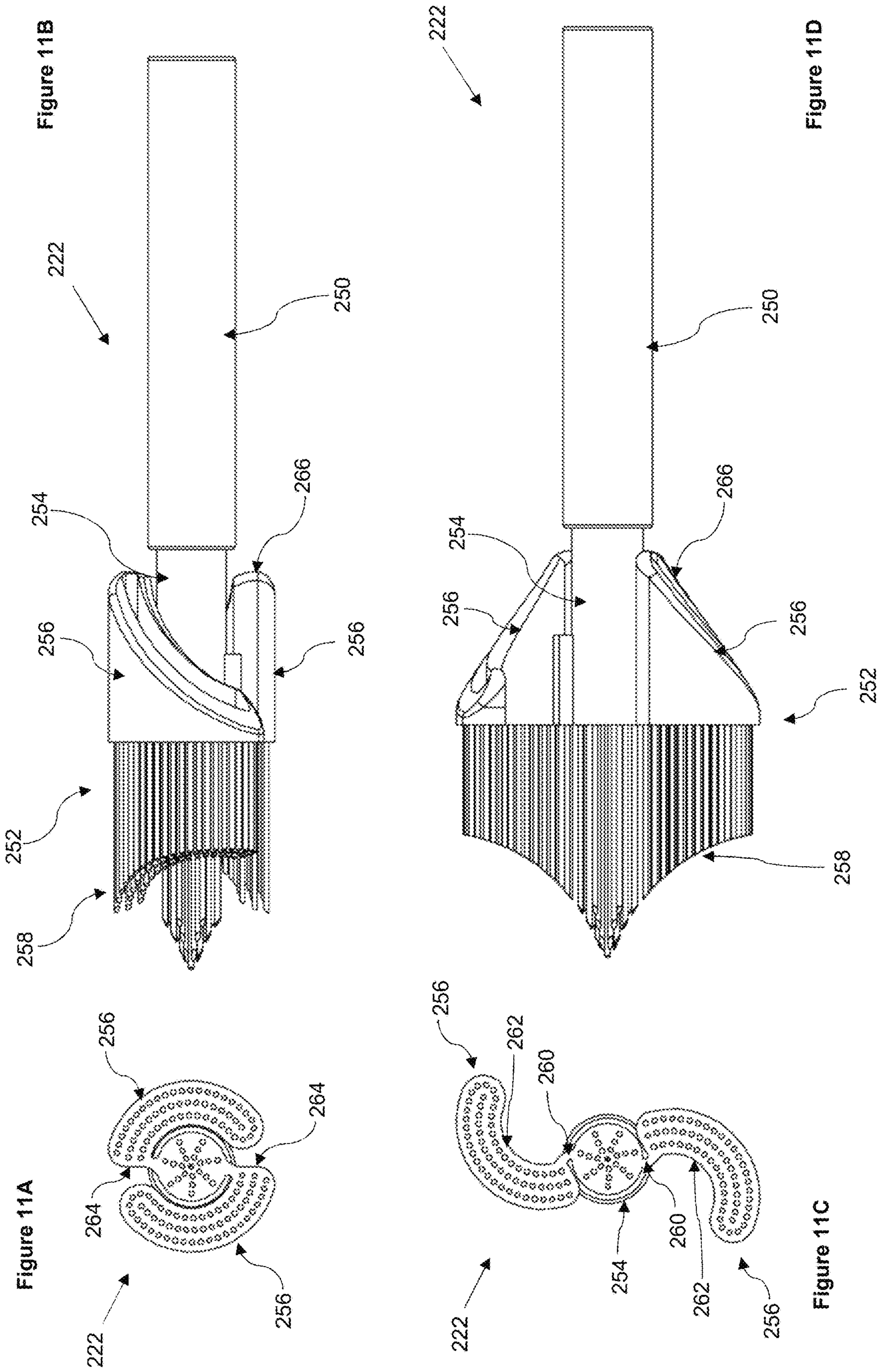
FIG. 11A shows an end view of the cervical sampling brush of FIG. 7.
FIG. 11B shows a side view of the cervical sampling brush of FIG. 11A.
FIG. 11C shows an end view of the cervical sampling brush in FIG. 9.
FIG. 11D shows a side view of the cervical sampling brush of FIG. 11C.

In the closed condition, as is the case in FIGS. 11A and 11B, the inner surfaces 262 of the lateral supports 256 matingly meet with an outer surface of the central hub 254, and the approximate cross-section of the cervical sampling head 252 is circular.

In the open condition, as is the case in FIGS. 11C and 11D, the end surfaces 264 of the lateral supports 256 matingly meet with the outer surface of the central hub 254 instead, and thus the approximate cross-section of the cervical sampling head 252 becomes sinusoidal or serpentine.

The hinge axes are not centrally positioned on said end surfaces 264, thereby ensuring ease of movement of the lateral supports 256.

Figure 12A:
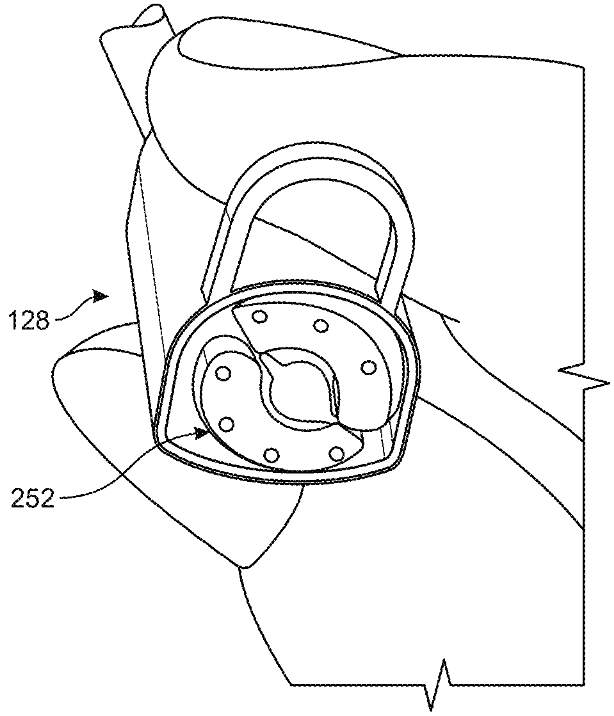
FIG. 12A shows a perspective representation of a cervical sampling head of the cervical sampling brush of FIG. 7, interacting with a brush housing of a cervical inspection device, in a retracted state.
Figure 12B:
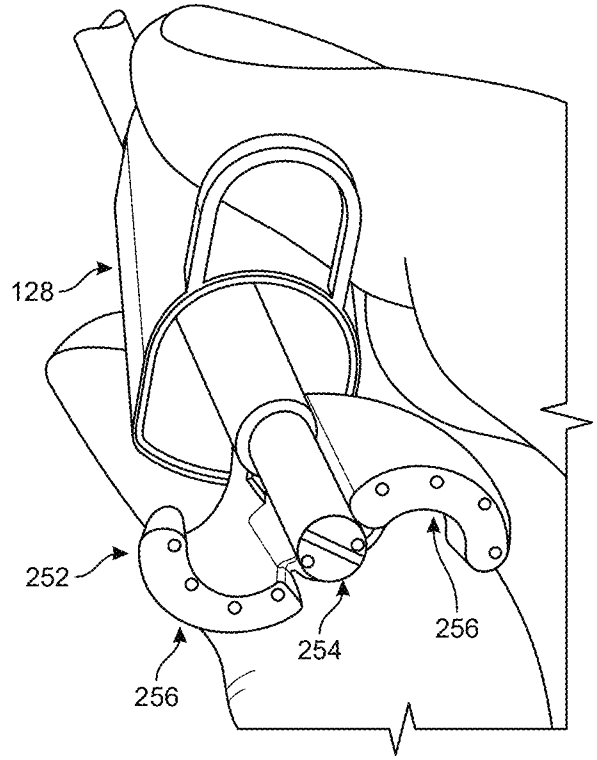
FIG. 12B shows a perspective representation of the cervical sampling head and brush housing of FIG. 12A, in an extended state.
Figures 16A, 16B, 16C, 16D:
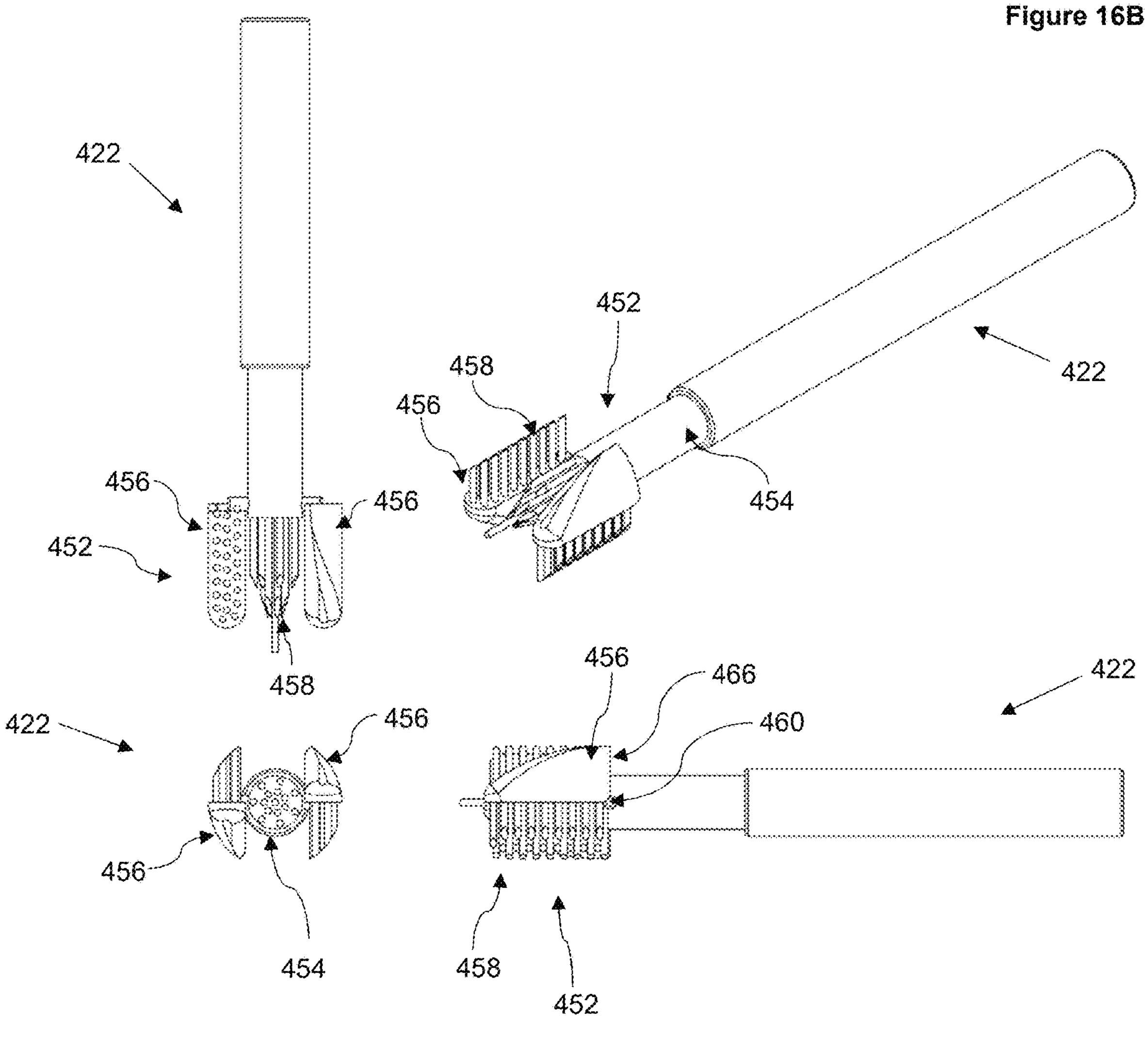
FIG. 16A shows a plan view of the cervical sampling brush of FIG. 15A, in a retracted state.
FIG. 16B shows a perspective view of the cervical sampling brush of FIG. 16A.
FIG. 16C shows an end view of the cervical sampling brush of FIG. 16A.
FIG. 16D shows a side view of the cervical sampling brush of FIG. 16A.

The lateral supports 256 in the present embodiment are arcuate, and more preferably rotationally symmetric, when viewed along the longitudinal axis of the cervical sampling brush 222, which allows them to curl in a spiral fashion towards the central hub 254 on folding. The bristle-distal edges 266 of the lateral supports 256 may preferably be tapered so that, upon contact with the outer rim 148 of a cervical inspection device 110, the lateral supports 256 are urged into the closed condition gradually. In the illustrated embodiment, the bristle-distal edges 266 also include a recess 268 or groove which could be used to guide the lateral supports 256 into or out of the closed condition. This process is shown in FIGS. 12A and 12B, with the bristles having been omitted from the cervical sampling head 252 for clarity. For the cervical sampling head 252 shown, a twisting action which accompanies the longitudinal urging of the cervical sampling brush 222 may help to encourage closure, by rotating the central hub 254 to encourage the hinges 260 to follow and thus fold up the lateral supports 254.

The bristle-distal edges 266 contact with the outer rim 148 of the brush housing 128, with the hinge member 260 resiliently moving depending on the force applied to the bristle-distal edges 266 by said outer rim 148. Thus, the motion of the cervical sampling brush 222 alone, be that by axial or axial and rotational action, causes the opening and closing of the cervical sampling head 252 and no additional control mechanism is necessary.

On retraction of the cervical sampling brush 222, the bristles 258 remain parallel with one another during the folding process, and as such, there is minimal risk of loss of sample by collision of the bristles 258 with one another or the central bore 120 of the cervical inspection device 110. There is therefore no risk of the bristles 258 becoming contaminated by the cervical inspection device 110 itself.

To use the cervical inspection device 110 with the cervical sampling brush 222, the medical practitioner inserts the cervical inspection device 110 into the patient's vaginal canal. The camera 140 is used to find and locate the cervical os and the likely transformation zone area of the cervix, once the cervical inspection device 110 has been inserted. The expansion element 130 can then be operated to urge the walls of the vaginal canal out of the way at the transformation zone, providing visual access for the camera 140 through the protection region thus formed. The cervical inspection device 110 can then be reoriented where required, based on the output of the camera 140.

Once the cervical inspection device 110 is correctly oriented, the cervical sampling brush 222 can be advanced by the medical practitioner towards the cervix. Upon leaving the central bore 120, the cervical sampling head 252 opens, with the force on the lateral supports 256 no longer being present from the brush housing 128. The resiliently flexible hinge members 260 open the lateral supports 256 into the open condition. The cervical sampling brush 222 can then be urged towards the transformation zone to collect a sample with the bristles 258.

Once sufficient sample is collected, the cervical sampling brush 222 can be retracted towards the cervical inspection device 110. Upon contact of the bristle-distal edges 266 with the outer rim 148 of the cervical inspection device 110, the taper of the bristle-distal edges 266 will gradually urge the lateral supports 256 towards the central hub 254. The cervical sampling head 252 thus closes up to itself to be receivable into the central bore 120.

Upon removal of the cervical sampling device 110 from the patient, the medical practitioner can remove the sheath 126 and brush housing 128 as one, to allow the tubular body 112 to be sanitized. The brush housing 128, containing the sampled-filled cervical sampling brush 222, can then be sent onwards for cytological analysis. Alternatively, the brush 222 can be extracted from the device 110, and the sheath 126 and brush housing 128 disposed of. Of course, it is equally feasible to extract the cervical sampling brush 222 on its own first, before washing in a cytology solution to be sent to a laboratory.

For some cytological analysis approaches, there is a requirement for the cervical sampling brush 222 to have a removable cervical sampling head 252 which can be transferred separately from the stem and/or handle of the brush in a cytology solution. This is anticipated as being feasible within all embodiments of the present invention.

FIGS. 13A to 14D show a second detailed embodiment of cervical sampling brush 322. Identical or similar features of the first embodiment will be referenced using identical or similar reference numerals, and further detailed description will be omitted for brevity.

The cervical sampling head 352 comprises a pair of diametrically opposed lateral supports 356 which are respectively connected to the central hub 354 at hinge members 360. The hinge axes of the hinge members 360 are parallel to one another, and as such, the two lateral supports 356 fold towards one another so as to overlie the bristles 358 of the central hub 354. The lateral supports 356 are formed as linear supports, having tapered bristle-distal edges 366 to close in a similar manner to the first brush embodiment.

Whilst the closing of the cervical sampling head 352 in this second embodiment brings bristles 358 into contact with one another, the closing mechanism may better protect the sample following extraction of the cervical sampling brush 322 from the patient, since the bristles 358 are no longer exposed. The risk of contamination decreases, reducing the risk of needing to reperform the cervical smear test.

FIGS. 15A to 16D show a third detailed embodiment of cervical sampling brush 422. Identical or similar features of the first and second embodiments will be referenced using identical or similar reference numerals, and further detailed description will be omitted for brevity.

The cervical sampling head 452 comprises a pair of diametrically opposed lateral supports 456 which are respectively connected to the central hub 454 at hinge members 460. The hinge axes of the hinge members 460 are co-axial and perpendicular to the longitudinal axis, and as such, the two lateral supports 456 fold towards one another without contacting one another. The lateral supports 456 remain spaced apart from one another either side of the central hub 454. The lateral supports 456 are formed as linear supports, having tapered bristle-distal edges 466 to close in a similar manner to the first and second brush embodiments.

Unlike the previous two embodiments, the hinge member 460 is here not formed as a resiliently flexible hinge, but as a continuous axle which extends through the cervical sampling head 452. Whilst a resiliently flexible hinge could be considered, a specific axle is less likely to break under the increased rotational stress.

FIGS. 17A to 18D show a fourth detailed embodiment of cervical sampling brush 522. Identical or similar features of the first, second, and third embodiments will be referenced using identical or similar reference numerals, and further detailed description will be omitted for brevity.

The cervical sampling head 552 comprises a pair of diametrically opposed lateral supports 556 which are respectively connected to the central hub 554 at hinge members 560. The hinge axes of the hinge members 560 are parallel to one another, and as such, the two lateral supports 556 fold towards one another so as to overlie the bristles 558 of the central hub 554. The lateral supports 556 are formed as fan-shaped supports which may allow novel bristle 558 configurations to be used which can better capture a wider area beyond the transformation zone during the cervical smear test.

Again, whilst the closing of the cervical sampling head 552 in this fourth embodiment brings bristles 558 into contact with one another, the closing mechanism may better protect the sample following extraction of the cervical sampling brush 522 from the patient, since the bristles 558 are no longer exposed. The risk of contamination decreases, reducing the risk of needing to reperform the cervical smear test.

FIGS. 19A to 20B show a further embodiment of a cervical inspection device, referenced globally at 610. Identical or similar features of the previous embodiments will be referenced using identical or similar reference numerals, and further detailed description will be omitted for brevity. It will be apparent that any or all of the features of this or the preceding devices, could be interchanged with one another within the scope of the overarching invention.

The cervical inspection device 610 has a tubular body 612 formed in two parts, having the central bore 620 running through the whole tubular body 612. There is a leading portion 668 within which is located a moveable brush housing 628, and a trailing portion 670 which includes the control means for the expansion element 630. It may be possible to provide the leading portion 668 as a disposable unit, which can be jettisoned after use and replaced with a sterile new leading portion 668 for the next patient.

The control means is here formed as a rotary member 672 formed on the tubular body 612 via which an internal screw thread 674 in the tubular body 612 can be driven to advance or retract the brush housing 628. The cervical sampling brush 622 can, however, be advanced or retracted by the operator separately to the movement of the brush housing 628.

Figures 19A, 19B:
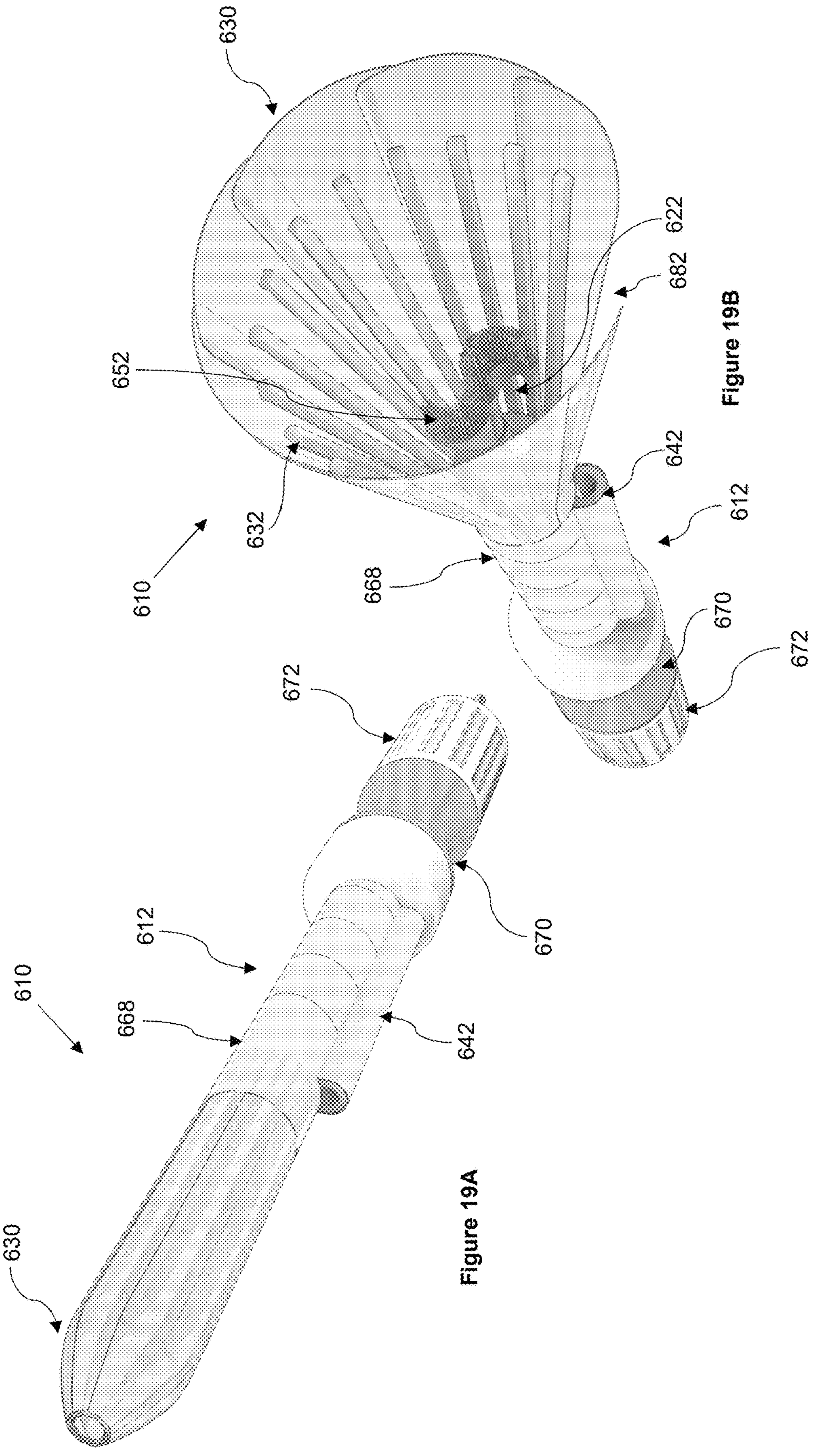
FIG. 19A shows a front perspective representation of a further embodiment of a cervical inspection device in accordance with the second aspect of the invention for performing a cervical smear test, in a retracted condition.
FIG. 19B shows a front perspective representation of the cervical inspection device of FIG. 19A, in an expanded condition.
Figures 20A, 20B:
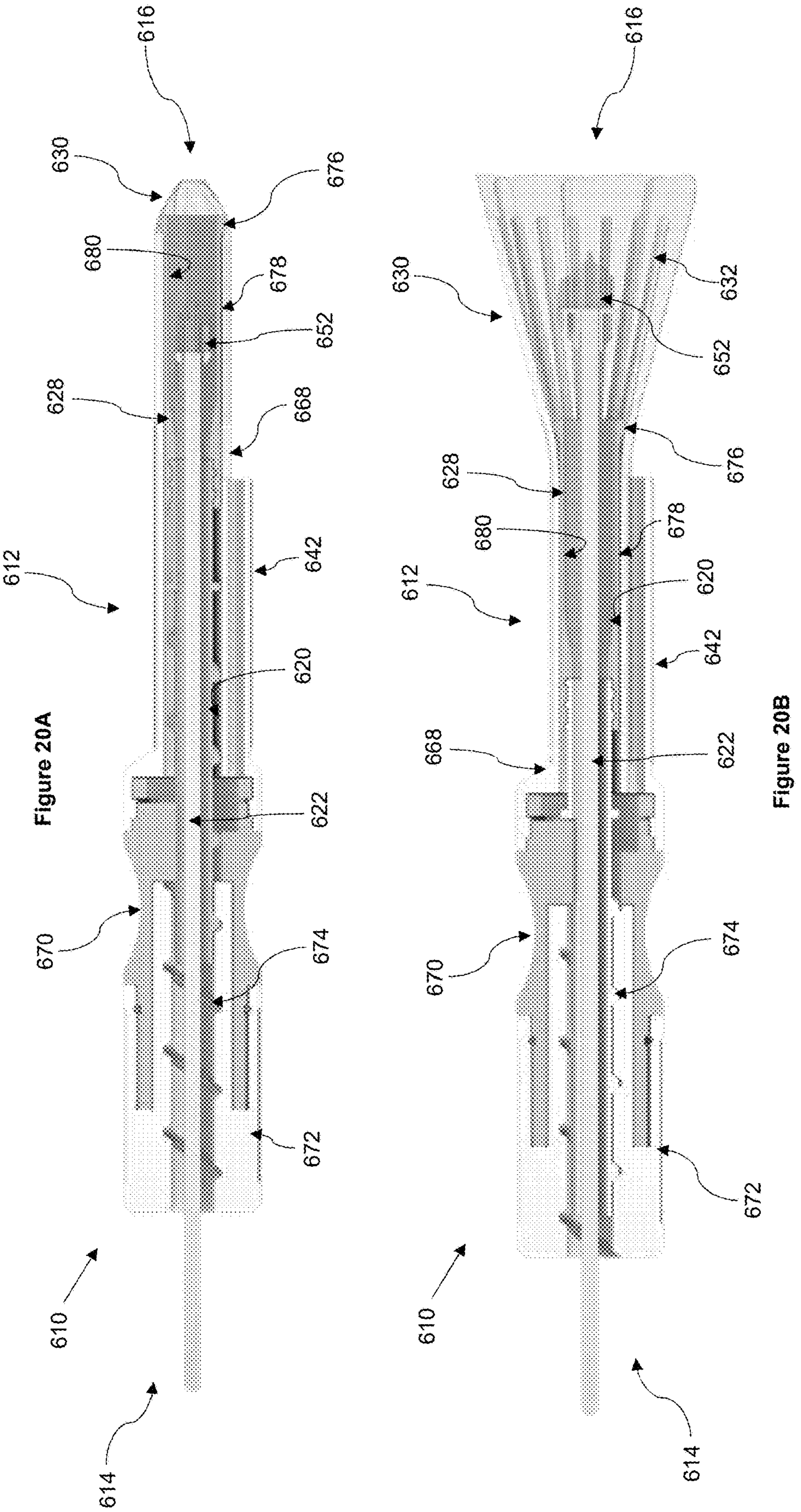
FIG. 20A shows a longitudinal cross-sectional representation of the cervical inspection device of FIG. 19A.
FIG. 20B shows a longitudinal cross-sectional representation of the cervical inspection device of FIG. 19B.

The expansion element 630 is formed as a hooded portion which splays into or substantially into the shape of a cone when activated. There is a plurality of tabs 632 positioned at the second end 616 of the cervical inspection device 610 which are splayed when there is an interference fit formed with an end of the brush housing 628 in the expanded condition. This occurs when the brush housing 628 has been withdrawn towards the first end 614 of the tubular body 612. An engorged lip 676 of the brush housing 628, which overhangs a primary outer wall 678 thereof, causes the interference expansion to occur, splaying the tabs 632 outwardly, as best seen in FIGS. 19B and 20B. The hooded portion is here shown as being a fluted paper hood, and a fluted structure may prove straightforward to allow for expansion and retraction.

Before use, the cervical sampling brush 622 is completely concealed within the brush housing 628, which is advanced towards the second end 616 of the tubular body 612. The cervical sampling brush 622 is kept in an unfurled condition by the internal walls 680 of the brush housing 628. As the brush housing 628 is withdrawn, the cervical sampling brush 622 is uncovered, and it unfurls. A cervical sampling brush 622 akin to that of FIGS. 11A to 11D is illustrated. The positioning of the cervical sampling brush 622 is such that, splaying of the tabs 632 occurs before complete release of the cervical sampling head 652, and thus the expansion element 630 is splayed sufficiently before unfurling of the cervical sampling brush 622, so that the cervical sampling head 652 never contacts the expansion element 630. The expansion element 630, in the expanded condition, thus forms a protective region around the cervical sampling brush 622, so that it can in-use be advanced towards the cervix without the cervical sampling brush 622 ever needing to be exposed to the vaginal canal.

Targeted sampling of the transformation zone of the cervix can thus be achieved without contamination, with the camera being positioned within the radial extent of the expansion element 630 once expanded. The camera, indicated here by the presence of a camera receiving area 642, allows for inspection of the transformation zone through the protective region. The camera could itself be positioned within the protective region formed by the expansion element 630, or there could be a viewing corridor 682 in the protective region, as illustrated.

It will be appreciated that, although the cervical inspection device has been described for use with a cervical sampling brush, the device has a wide utility in cervical sampling contexts. In particular, there are other cervical inspection tools which are available which could be inserted through the central bore of the device, such as a sprayer suitable for spraying acetic acid onto the transformation zone in order to improve the identification of cellular markers. The brush housing which forms the central bore as herebefore described thus could readily be any cervical inspection tool housing, which could be disposed after use.

It is therefore possible to provide a generalised method of controlling a cervical inspection device for performing a cervical smear test, the method comprising the steps of: providing a cervical inspection device as previously described; pushing the cervical sampling brush through the central bore of the tubular body to permit opening of the cervical sampling head into the sampling condition; and pulling the cervical sampling brush into the central bore of the tubular body to urge the lateral supports of the cervical sampling brush to fold towards the central hub upon contact of the lateral supports with the tubular body. Regardless of which brush type is used, the folding mechanism can be achieved, and a less stressful cervical smear test completed for the patient.

The presence of a camera and the engagement elements to allow for improved inspection of the cervical transformation zone is a significant advance over the state of the art, reducing the risk of discomfort to the patient, particularly those patients with retroverted uteruses. Irrespective of the brush or swab used, the present invention therefore also provides for a cervical inspection device for performing a cervical smear test, or other cervical inspection techniques, the device comprising: a tubular body having a first end which is engagable by an operator and a second end which is insertable into a patient's vaginal canal, the tubular body having a central bore which extends along its longitudinal axis; a cervical brush or swab insertable through the central bore of the tubular body; an expansion element at or adjacent to the second end of the tubular body; control means operable from the first end of the tubular body for selectably expanding and/or contracting the expansion element; and a camera at or adjacent to second end of the tubular body and which is positioned radially outwardly of the central bore. This achieves the aim of reduced-pain cervical smear testing, eliminating the need for a speculum.

Overall, the present invention provides a means of improving the overall experience of the cervical smear test for women, hopefully improving uptake, and reducing the risk of sample contamination.

The words 'comprises/comprising' and the words 'having/including' when used herein with reference to the present invention are used to specify the presence of stated features, integers, steps, or components, but do not preclude the presence or addition of one or more other features, integers, steps, components, or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The embodiments described above are provided by way of examples only, and various other modifications will be apparent to persons skilled in the field without departing from the scope of the invention as defined herein.

The invention claimed is:

1. A cervical inspection device for performing a cervical smear test, the device comprising:

a tubular body having a first end which is engagable by an operator and a second end which is configured to be insertable into a patient's vaginal canal, the tubular body having a central bore which extends along its longitudinal axis for receiving a cervical sampling brush therethrough;

an expansion element at the second end of the tubular body; and control means operable from the first end of the tubular body for selectably expanding and/or contracting the expansion element; and characterised by the expansion element is expandable and/or contractable at the second end of the tubular body without altering a dimension of the tubular body, the expansion element forming a circumferentially-bound protective region beyond the central bore in an expanded condition thereof for the cervical sampling brush to move through during the cervical smear test, and further comprising a camera at or adjacent to the second end of the tubular body and positioned radially outwardly of the central bore and radially inward of the expansion element.

2. The cervical inspection device as claimed in claim 1, wherein the tubular body comprises a brush housing which includes a channel forming the central bore.

3. The cervical inspection device as claimed in claim 2, wherein the brush housing is removable from the tubular body.

4. The cervical inspection device as claimed in claim 1, wherein the tubular body is a two-part body having a leading portion which is removable from a trailing portion.

5. The cervical inspection device as claimed in claim 2, further comprising a camera receiving area at or adjacent to an end of the channel which is laterally spaced apart from the central bore and within a maximum lateral extent of the expansion element in the expanded condition.

6. The cervical inspection device as claimed in claim 1, wherein the camera is angled towards an axis of the central bore for monitoring the cervical sampling brush in use.

7. The cervical inspection device as claimed in claim 1, further comprising an illumination element associated with the camera.

8. The cervical inspection device as claimed in claim 1, wherein the expansion element has a conical, frusto-conical, substantially conical, or substantially frusto-conical shape in the expanded condition.

9. The cervical inspection device as claimed in claim 1, wherein a distal rim of the expansion element in-use forms a cervical-proximal edge of a protection zone to form an enclosure with a cervix.

10. The cervical inspection device as claimed in claim 1, wherein the expansion element comprises a flexible hood, the control means comprising a plurality of tabs for urging the flexible hood into an open condition.

11. The cervical inspection device as claimed in claim 1, further comprising a sheath which is receivable over the tubular body.

12. The cervical inspection device as claimed in claim 1, wherein the expansion element is dimensioned to form the circumferentially-bound protective region in-use around a cervix to be inspected in the expanded condition.

13. The cervical inspection device as claimed in claim 1, further comprising the cervical sampling brush comprising:

an elongate stem; and a cervical sampling head having a central hub and a lateral support, the cervical sampling head having a plurality of flexible sampling bristles thereon;

wherein in a sampling condition, the lateral support has a first lateral extent relative to the elongate stem, and in a retraction condition, the lateral support is movable or foldable towards an axis of the elongate stem to adopt a second lateral extent which is less than the first lateral extent, so as to be receivable into the tubular body without the plurality of flexible sampling bristles contacting the tubular body or the expansion element.

14. The cervical inspection device as claimed in claim 13, wherein the lateral support of the cervical sampling brush is engaged to the central hub via a hinge member.

15. The cervical inspection device as claimed in claim 13, wherein the lateral support or each lateral support has a tapered bristle-distal edge to urge the lateral support or each lateral support into the retracted condition upon application of an axial force.

16. The cervical inspection device as claimed in claim 13, wherein the central bore is at least in part dimensioned to receive the cervical sampling brush therethrough when the cervical sampling head is in the retracted condition.

17. The cervical inspection device as claimed in claim 13, wherein an operation of the control means is independent of a movement of the cervical sampling brush.

18. A method of controlling the cervical inspection device for performing the cervical smear test, the method comprising:

providing the cervical inspection device as claimed in claim 1, the expansion element being in a contracted condition; and using the control means, expanding the expansion element into the expanded condition to a protective region beyond the central bore through which the cervical sampling brush passes.

19. A cervical inspection device for performing a cervical smear test, the device comprising:

a tubular body having a first end which is engagable by an operator and a second end which is configured to be insertable into a patient's vaginal canal, the tubular body having a central bore which extends along its longitudinal axis for receiving a cervical sampling brush therethrough;

an expansion element at the second end of the tubular body; and control means operable from the first end of the tubular body for selectably expanding and/or contracting the expansion element; and characterised by the expansion element is expandable and/or contractable at the second end of the tubular body without altering a dimension of the tubular body, the expansion element forming a circumferentially-bound protective region beyond the central bore in an expanded condition thereof for the said cervical sampling brush to move through during the cervical smear test, and further comprising the cervical sampling brush comprising:

an elongate stem; and a cervical sampling head having a central hub and a lateral support, the cervical sampling head having a plurality of flexible sampling bristles thereon;

wherein in a sampling condition, the lateral support has a first lateral extent relative to the elongate stem, and in a retraction condition, the lateral support is movable or foldable towards an axis of the elongate stem to adopt a second lateral extent which is less than the first lateral extent, so as to be receivable into the tubular body without the plurality of flexible sampling bristles contacting the tubular body or the expansion element.

* * * * *